(12) United States Patent
Ahlnas

(10) Patent No.: US 8,496,974 B2
(45) Date of Patent: Jul. 30, 2013

(54) METHOD FOR PREPARING A COMPOSITION COMPRISING A COMPOUND MIXTURE AND A CARRIER AGENT

(75) Inventor: Thomas Ahlnas, Kotka (FI)

(73) Assignee: Oy Granula AB Ltd, Kotka (FI)

( * ) Notice: Subject to any disclaimer, the term of this patent is extended or adjusted under 35 U.S.C. 154(b) by 0 days.

(21) Appl. No.: 12/626,063

(22) Filed: Nov. 25, 2009

(65) Prior Publication Data

US 2010/0129304 A1    May 27, 2010

Related U.S. Application Data

(60) Provisional application No. 61/117,702, filed on Nov. 25, 2008.

(51) Int. Cl.
*A01N 65/00* (2009.01)

(52) U.S. Cl.
USPC ............................................. 424/725

(58) Field of Classification Search
None
See application file for complete search history.

(56) References Cited

U.S. PATENT DOCUMENTS

2005/0169947 A1* 8/2005 Korte et al. ................. 424/401

FOREIGN PATENT DOCUMENTS

| WO | WO 2004/000304 A1 | | 12/2003 |
| WO | WO 2005/047423 | * | 5/2005 |
| WO | WO 2005/047423 A1 | | 5/2005 |
| WO | WO 2007/096089 A1 | | 8/2007 |
| WO | WO 2007/096090 A1 | | 8/2007 |
| WO | WO 2007/096088 A1 | | 9/2007 |
| WO | WO 2008/020112 A1 | | 2/2008 |

OTHER PUBLICATIONS

Anna-Liisa Valimaa et al., "Antimicrobial and cytotoxic knotwood extracts and related pure compounds and their effects on food-associated microorganisms", International Journal of Food Microbiology, 2007, pp. 235-243, vol. 115, Elsevier.

Bjarne Holmhbom et al., "Knots in trees—A new rich source of lignans", Phytochemistry Reviews, 2003, pp. 331-340, vol. 2.

* cited by examiner

*Primary Examiner* — Michael Meller
(74) *Attorney, Agent, or Firm* — Young & Thompson

(57) ABSTRACT

In a method for preparing a composition including a compound mixture and a carrier agent, the compound mixture is obtained by pulverizing the wood material and/or by extracting the wood material so that the compound mixture contains at least two different compounds, selected from a first specified group, at least one compound selected from a second specified group, the compound mixture is mixed with the carrier agent, the amount of the compound mixture is kept in a range of 0.1-5 wt % from the total weight of the composition, providing that the range is also such that the total cytotoxicity of compound mixture dissolved in ethanol, measured for a HaCat cell culture after 24 h incubation period, is lower than the cytotoxicity of 0.02-0.1 wt % butylated hydroxy toluene (BHT) dissolved in ethanol for a HaCat cell culture after 24 h incubation period.

42 Claims, No Drawings

METHOD FOR PREPARING A COMPOSITION COMPRISING A COMPOUND MIXTURE AND A CARRIER AGENT

RELATED APPLICATIONS

This application is based on provisional application No. 61/117,702 filed on 25 Nov. 2008.

TECHNICAL FIELD

The invention relates to methods for preparing a composition comprising a compound mixture and a carrier agent.

BACKGROUND

Sunlight contains both UVA radiation, with a wavelength of 320-400 nm, and UVB radiation, with a wavelength of 280-320 nm. Both UVA and UVB radiation have detrimental cytotoxic effects on skin cells, but with different effect mechanisms. UVB radiation directly induces mutations and damages in the DNA of skin cells. As for UVA radiation, it induces the creation of reactive free radicals on the skin surface from coumarin-type compounds. Thereafter said free radicals can damage skin cells, thus predisposing the skin to various cancer diseases. The effect of UVB is inhibited by protecting the skin with sun protective compositions containing UV filtering agent that transfers UVB radiation into a form that is harmless to skin cells, such as heat or long-wave radiation. The effect of UVA radiation is inhibited by UV filters (UV protection agents) that are capable of trapping free radicals induced by sunlight.

Both inorganic and organic compounds are used in sun protective compositions as UV protection agents, to prevent the detrimental effect on skin cells of UV radiation contained in sunlight. They either absorb and reflect UV radiation within a relatively narrow wavelength range, or alternatively capture free radicals induced by UV radiation, such as oxygen, hydroxyl or peroxide radicals.

Inorganic UV filters (below also inorganic UV protection agents) are finely divided (10-100 nm) inorganic mineral pigments, such as $TiO_2$, ZnO and $Fe_xO_y$, which reflect or absorb UV radiation.

Among the compounds used in organic sun protective compositions and serving mainly as UVB protection agents, absorbing UVB radiation, are for example octyl triazine, urocanic acid, octyl methoxy cinnamate, methylbenzylidene camphor, 3-benzylidene sulphonic acid and PABA i.e. octyl dimethyl, 4-aminobenzoic acid (para-aminobenzoic acid).

Typical UVA radiation inhibitors used in sun protective compositions, functioning by the free radical trapping mechanism, are organic aromatic compounds containing conjugated carbonyl groups. Among these are for example benzophenon-3, benzophenon-4 butyl methoxydibenzoyl-methane and terephtalyliden sulphonic acid. Said aromatic compounds protect the DNA of skin cells by preventing conjugated DNA double bonds from absorbing UV radiation both within the UVA range (320-360 nm) and also within the UVB range (280-320 nm).

At present, there are also available organic UV protection agents that are capable of absorbing UV radiation both within the UVA range and the UVB range. This kind of agent is for example MBBT.

Antioxidants are often added in sun protective compositions in order to prevent the oxidation of the compounds contained in the composition and to capture the possibly created oxygenous reactive compounds and free radicals. Also in foodstuffs there are used antioxidants that are capable of neutralizing, i.e. trapping oxygenous free radicals created through the auto-oxidation of foodstuffs, such as peroxide radicals. Thus they slow down the auto-oxidation process of food, preventing changes in the color, smell and taste of food. Among these antioxidants, there are natural vitamins such as A, B, C, D and E vitamins, and synthetic vitamins such as the above mentioned analog of vitamin B, i.e. para-aminobenzoic acid, the synthetic phenolic analog of vitamin E, BHT, i.e. 2,6-(bis)-(1.1-dimethylethyl)-4-methylphenyl (butylated hydroxy toluene) and BHA (butylated hydroxy anisole, which is a mixture of two isomeric organic compounds, containing 2-tert-butyl-4-hydroxy anisole and 3-tert-butyl-4-hydroxy anisole. The antioxidants used in foodstuffs and sun protective compositions may in certain conditions be cytotoxic to the human organism. Among these, there are also BHT (foodstuff additive E321) and BHA, which means that their use is restricted, and they cannot be sufficiently added to the target of usage in order to ensure their antioxidative effect.

Certain organic UV protection agents or inorganic mineral compounds used for absorbing UV radiation may, however, spontaneously release free radicals owing to the effect of UV radiation, or they may induce the creation of free radicals in the target of usage. Among free radicals, let us mention for example hydroxyl radicals, peroxide radicals, unimolecular oxygen, and temporary lipid radicals. When penetrating to the human system, free radicals may cause cytotoxic exposure.

Consequently, compounds used in sun protection agents may, owing to the effect of UV radiation, spontaneously release free radicals. As was pointed out above, in sun protective compositions there are generally used inorganic UV protection agents $TiO_2$ and ZnO, $CeO_2$, which absorb UV radiation within a wide wavelength range. However, inorganic UV filters have a strong tendency to be agglomerated owing to the effect of electrostatic forces, which means that their efficiency is drastically reduced. Therefore said finely divided inorganic pigments must be coated with silica or aluminum compounds and dispersed in a solvent, such as dispersion oil, for example in isononyl-isononanoate or dimethicone, in the presence of suitable surface active agents. Coated inorganic UV-filter mediums may themselves turn cytotoxic; in aqueous conditions, they may induce the creation of hydroxyl radicals on the skin, in case their protective coating layer is worn off. They may also themselves turn into reactive radicals, in case there are holes in their coating, or if the coating is worn off.

In the course of time, several organic UV protection agents, such as PABA, OMC and Octocrylene, gradually penetrate into the skin. In case the sun protective composition is not reapplied on the skin, or if the layer applied on the skin is otherwise worn off, there are created monoatomic reactive oxygen radicals owing to the effect of UV light. It has also been found that benzophenon-3, a UV filter generally used in sun protection agents, also penetrates into the system through the skin, which means that it may itself induce the creation of free radicals deeper in the system.

It is often necessary to add microbicidic agents into cosmetic compositions and technical solvents and cleaning agents as well as industrially used solvents. Microbicidic agents may be cytotoxic or otherwise detrimental to the system when getting into contact with the skin.

OBJECT OF THE INVENTION

The object of the invention is to eliminate the above described drawbacks of the prior art.

Thus, the principal object of the invention is to realize a composition and a method for producing said composition, wherein the unwanted properties of the effective agent contained in the composition, such as UV protection agent, are reduced, or the action of the composition has changed. Unwanted properties are for example cytotoxicity of the agent, as well as its tendency to form or induce free radicals on the skin, skin irritation. One example of the changing of the action of the effective agent in composition is that the in vitro protective factor of the composition containing UV protection agent has remained the same, while its protective factor in vivo has raised. Further, the principal object of the invention is to realize compositions or semifinished compositions used in the production of said compositions, where the effective agent or part of it is obtained from nature.

A further object of the invention is to reduce the detrimental properties of the effective agent contained in the composition by using a mixture that has good availability and low manufacturing expenses.

Free radical here refers to a molecule or an atom that has unpaired electrons in its electron shell. Typical free radicals are oxygen radical, hydroxyl radical and peroxyl radicals as well as superoxide radicals, but also for example lipid radicals. Further, for instance titanium oxide can be formed into a reactive free radical, in case it is tuned to a higher energy state owing to the effect of UV radiation. A compound is called free radical capturer, in case it is capable of inhibiting the creation of free radicals, or their function. In case the compound is capable of inhibiting the creation of oxygenous free radicals and their effects, the compound is called antioxidant.

GENERAL DESCRIPTION OF THE INVENTION

The invention relates to method for preparing a composition comprising a compound mixture and a carrier agent, wherein the compound mixture is obtained by pulverizing the wood material and/or by extracting the wood material so that said compound mixture contains at least two different compounds, selected from the group consisting of: lignans, stilbenes, juvabiones, flavonoids, betulin, betulonic acid, betulinic acid, and betuloinic acid, and ester derivatives or ether derivatives or stereoisomers of said compounds said compound mixture containing also oligomers of lignans or stilbenes or juvabiones or flavonoids; providing that the compound mixture contains lignans or ester derivatives or ether derivatives or stereoisomers thereof 50-99.9 wt %, oligomers of lignans or stilbenes or juvabiones or flavonoids 1-31 wt %, at least one compound selected from the group consisting of: 7-hydroxymatairesinol, conidendrin, conidendric acid, alpha-conidendrin, alpha-conidendric acid, isohydroxymatairesinol, cyclolariciresinol, secoisolariciresinol, anhydrosecoisolariciresinol and stilbenes as well as their ester or ether derivatives and stereoisomers, the compound mixture is mixed with the carrier agent, the amount of the compound mixture is kept in a range of 0.1-5 wt % from the total weight of the composition, providing that the range is also such that the total cytotoxicity of compound mixture dissolved in ethanol, measured for a HaCat cell culture after 24 h incubation period, is lower than the cytotoxicity of 0.02-0.1 wt % butylated hydroxy toluene (BHT) dissolved in ethanol for a HaCat cell culture after 24 h incubation period.

Especially in the composition, there is included a carrier agent conventionally used in a cosmetic composition, food industry composition, animal feed composition, technical composition or packing material composition, possible auxiliary agents and possible surface active agent, as well as an effective agent, which is selected among the following group: antimicrobial agent, UV protection agent, antioxidant, or capturer of free radicals. Further, in the composition, there is included a compound mixture for modifying the properties of the effective agent, which compound mixture is obtained by pulverizing wood material from two different wood species and/or by extracting the possibly pulverized wood material from two different wood species, so that said compound mixture contains at least two different compounds selected from among the following group: lignans according to general formulas IA and IB, stilbenes according to general formula II, juvabiones according to general formula III, flavonoids according to general formula IV and betulin and its derivatives (betulinic acid, betuloinic acid or betulonic acid), said compound mixture also containing oligomers of said polyphenolic compounds, providing, however, that the compound mixture contains lignans according to formulas IA and IB, or their ether or ester derivatives or stereoisomers, particularly 7-hydroxymatairesinol or secoisolariciresinol, cycloisolariciresinol, anhydrosecoisolariciresinol, α-conidendrin, α-conidendric acid, isohydroxymatairesinol, or their ether and ester derivatives and stereoisomers for roughly 50-99.9 wt %; stilbenes according to formula II, particularly pinosylvin or its ester or ether derivatives for roughly 0.1-70 wt %; oligomers of lignans according to formula IA or IB, of stilbenes according to formula II, of juvabiones according to formula III or of flavonoids according to formula IV for roughly 1-31 wt %; providing, however, that the compound mixture contains at least one compound, selected from among the following group: 7-hydroxymatairesinol, secoisolariciresinol, cycloisolariciresinol, anhydroseco-isolariciresinol, α-conidendrin, α-conidendric acid, isohydroxymatairesinol and stilbenes according to formula II, as well as their ether and ester derivatives and stereoisomers.

Advantageously, in the composition, there is included said compound mixture for 0.1-5 wt % of the total weight of said composition, providing, however, that with said content, the compounds added in the composition do not irritate the skin in a so-called single patch test, and that the cytotoxicity of said compounds, measured as the cytotoxicity of compounds dissolved in ethanol with a HaCat cell culture after 24 incubations, is lower than the cytotoxicity of 0.02-0.1 wt % BHT dissolved in ethanol in the same incubation conditions, preferably lower than the cytotoxicity of 0.01-0.05 wt % BHT dissolved in ethanol in the same incubation conditions, in addition to which the compound mixture within said content range has properties for modifying the effect of the first effective agent in the target of usage.

Here the term stereoisomers refers to compound diastereomers and to mixtures of different diastereomers, to pure enantiomers and racemic mixtures of enantiomers.

The invention is based on the surprising observation that sufficient attention has previously not been paid to the level of overall cytotoxicity of the effective agents in cosmetic materials, foodstuffs, animal feed and packing materials, but each effective agent to be included in the composition, such as antioxidant, has been added to an extent that its maximum cytotoxicity by any means has allowed. With this observation in mind, the applicant has attempted to achieve compositions where the overall cytotoxicity of the different components of the effective agent is brought as low as possible, while the effect of the effective agent remains the same.

In the present invention, the optimizing of the overall cytotoxicity is realized by using an effective agent comprising compound mixture that is obtained from wood material by extracting and/or pulverizing and that is essentially unrefined. The mutual ratio between the phenolic compounds contained in said compound mixture, as well as the compounds contained in the compound mixture, can change depending on the effects required in the target of usage. The overall cytotoxicity of the compound mixture must, however, be as low as possible and remain below certain limits in comparison with the cytotoxicity of butylated hydroxytoluene BHT, irrespective of the phenolic compounds contained in the compound mixture. If the effective agent consists of compound mixture and an additional other effective agent (=first effective agent) the effective power and effective profile of the compound mixture are adjusted according to the target of usage of the composition, so that by using the compound mixture, the harmful properties of the first effective agent, such as its own cytotoxicity, can be remarkably reduced in the target of usage, such as on the skin or hairs of a mammal, for instance by reducing the quantity of the first effective agent from the conventionally applied level or trapping free radicals induced by the particles of the first effective agent. At the same time, the effective power and effective profile of the first effective agent are maintained the same or even expanded and modified by using a compound mixture that has, in addition to a low overall cytotoxicity, also a similar type of effective profile and effective power in the target of usage as the first effective agent. Apart from an effective profile similar to the first effective agent, the compound mixture often has other advantageous properties in the target of usage, so that by using this type of effective agent composed of a compound mixture and a first effective agent, the effective profile of the first effective agent contained in the composition can be modified.

The production method of the compound mixture is simple, and it is amply available from the pulping processes of wood processing industry, so that the replacing of the first effective agent by the compound mixture is economically feasible. Moreover, the compound mixture according to the invention has several other advantageous properties that its separate individual components do not necessarily have as such. The compound mixture according to the invention does not irritate the skin even with high contents, is physiologically well tolerated and has a low cytotoxicity. The lignans contained by the compound mixture are semipolar by nature, wherefore they can be included both in the aqueous and oil phases of the compositions.

In this connection, the modification of the effective profile of the first effective agent means that by means of the compound mixture, there are obtained additional properties in the composition, which properties are similar to the basic properties of the first effective agent. Among such additional properties are improvements in the UVA or UVB radiation absorbing efficiency of the UV protection agent, an increase in the in vivo sun protective factor (SPF) of the UV protection agent, improvements in the efficiency of antioxidants in trapping free radicals, etc.

As for reducing the harmful properties of the first effective agent, we mean that the unwanted properties of the first effective agent, such as cytotoxicity or skin irritation, tendency to form or induce free radicals in the environment of usage, etc., can be reduced.

The composition can be a cosmetic composition, a food industry composition, an animal feed composition, a technical composition, or a packing material.

The term 'cosmetic composition' here refers to compositions meant for the treatment of the skin, teeth, hair and body hair of mammals. In these, the carrier agent is a semisolid material such as cream, gel or paste; solid material such as solid foam; heterogeneous solid material or powder; liquid material such as homogeneous solution; colloidal as a dispersion or suspension; a microemulsion, a nanoemulsion, or a gaseous material such as aerosol or mist.

Food industry compositions here refer to both individual foodstuffs and foodstuff products. In this sense, food industry compositions are for example fruits, vegetables etc. individual foodstuffs, but also food industry products and semifinished products, in the preservation of which there are needed antimicrobial agents.

The packing material composition is a composition where the carrier agent is a packing material that is impregnated by a compound mixture according to the invention, in which there is spread the compound mixture according to the invention.

The technical composition is an agent where the carrier is a solvent used in cleaning, a cleaning device such as a cleaning cloth, solid material such as a powder used as a surface treatment agent; or the carrier agent is a solution meant for cleaning the body of a mammal. In the carrier, there is impregnated or otherwise included in the compound mixture according to the invention.

The manufacturing of the compound mixture is simple, and the compound mixture is amply available from wood industry pulping processes, so that the replacing of the effective agent by said compound mixture also is economically beneficial. The compound mixture according to the invention also has several other advantageous properties that its individual components do not necessarily have, so that by using the compound mixture, new properties can be obtained in the manufactured compositions. The compound mixture is advantageously an unpurified powder ground of wood material, or a compound mixture extracted from wood material in an extraction solution, said compound mixture forming a homogeneous solution, suspension or dispersion with the extraction solution. Even more preferably, the compound mixture is an unpurified lignan mixture and/or stilbene mixture placed in a liquid, said compound mixture containing at least two different lignan and/or stilbene compounds. The compound mixture is advantageously obtained by extracting wood material from two different wood species in an alcohol-based solution. Preferably the wood material is obtained from wood knot material or stemwood material from adjacent to knots.

Here the term unpurified or unrefined compound mixture refers to a compound mixture that is obtained by pulverizing and/or extracting wood or plant material, which mixture has thereafter not been subjected to any such chemical or physical cleaning operations by which one of the compound mixture compounds would be completely removed from the compound mixture. Typical cleaning operations in this sense are chromatography or crystallization of certain compounds from the solution. Instead, the compound mixture may be subjected to such chemical treatments by which the content of one of the compound mixture compounds is adjusted in relation to other compounds contained in the compound mixture. This kind of operation is for example extraction by which the mutual contents of the compounds contained in the solution are adjusted with respect to each other, but by which the compounds are not completely removed.

The polyphenolic compounds contained in the compound mixture may also be transformed into simple derivatives such as their esters, or into completely other stilbene/lignan/flavonoid compounds, when the pH of the extract solution is changed. The compound mixture to be included in the composition according to the invention, which mixture has free radical capturing properties, contains preferably at least two different phenolic compounds selected from the following groups:

Lignans:
matairesinol, hydroxymatairesinol, oxomatairesinol, didemethyl matairesinol, didemethyl matairesinol, isohydroxymatairesinol, epi-isohydroxymatairesinol and their stereoisomers, among which particularly let us point out hydroxymatairesinol stereoisomers 7S,8R, 8'R-hydroxymatairesinol and 7R,8R,8'R-allohydroxymatairesinol, and their stereoisomers and ester or ether derivatives, secoisolariciresinol, isolariciresinol, lariciresinol, pinoresinol, dimethyl secoisolariciresinol, 7-hydroxysecoisolariciresinol, cyclolariciresinol, cycloisolariciresinol, anhydrosecoisolariciresinol, alpha-conidendrin, alpha-conindendric acid, isohydroxymatairesinol and their stereoisomers as well as their ester or ether derivatives, nortrachelogenin and its stereoisomers and ester or ether derivatives, enterolactone and its stereoisomers and ester or ether derivatives, conidendrin, alpha-conindenrin and their stereoisomers as well as ester or ether derivatives, lignan A and its stereoisomers and ester or ether derivatives, liovile and its stereoisomers and ester or ether derivatives;

Juvabiones:
juvabiones and their stereoisomers and ester or ether derivatives;

Stilbenes:
pinosylvin, dihydropinosylvin, pinosylvin monomethyl ether, dihydropinosylvin monomethyl ether, resveratrol, astringin, isorhapontine, and their stereoisomers and ester or ether derivatives;

Flavonoids:
pinosembrin, catechin, pinobanxin, kaempferol, dihydrokaempferol, taxifolin, naringenin, teracasidine, ketoteracasidine, isoteracasidine, melacasidine, isomelacasidine and their stereoisomers and ester or ether derivatives;

Betulin, betulinic acid, betuloinic acid or betulonic acid and their stereoisomers and esterized forms,
as well as the glycosidized forms of these phenolic compounds, and their oligomers such as trimers and tetramers. These oligomers are here called oligolignans in case they are oligomers of lignans, stilbenes or juvabiones; free lignans and stilbenes are dimers, having 2 phenylpropane units coupled together by beta-beta bonds, and their oligolignans have 3-6 phenyl propane units ($C_6C_3$) coupled together by beta-beta bonds.

In this connection let us point out that compounds called lignans are generally (poly)phenolic compounds obtained from wood and plants, having 2 phenyl propane units coupled together by beta-beta bonds (IUPAC, 2000), but in this application it has been considered necessary to distinguish lignans, stilbenes and juvabiones from each other owing to their different microbiological effects.

Lignans proper here refers to compounds according to the general formula IA and IB (Appendix).

Now, in formula IA:
R1 or R2 denote, irrespective of each other, residue selected from the groups hydrogen, OH or =O,
or either one of the residues R1 or R2 denotes the oxygen atom —O— bound to carbons 9 and 9', and now forms with carbons 8, 8', 9, 9' a 5-membered oxygenous heterocyclic ring C,
R3 denotes hydrogen or residue selected from the group OH, =O, or it forms a bond to the carbon 6, so that the carbons 6, 1, 7, 8, 8', 7' form a cyclohexane ring that is condensed with the phenyl ring A, and possibly also a ring with C,
R4 denotes hydrogen or methyl,
R5 denotes hydrogen or residue selected from the groups OH and $OCH_3$,
R6 denotes hydrogen or hydroxy,
R7 and R8 denote, irrespective of each other, hydrogen or residue selected from the groups OH and $OCH_3$.

Advantageous lignans according to formula IA are:
7-hydroxymatairesinol (R1 denotes group =O, R2 denotes the oxygen atom pertaining to the hetero ring C, R4=$CH_3$, R7=$OCH_3$, R3=R5=R8=OH, R6=H, R9=H), matairesinol (R1 denotes group =O, R2 denotes the oxygen atom pertaining to the hetero ring C, R3=R6=R9=H; R4=$CH_3$, R7=$OCH_3$, R5=R8=OH), oxomatairesinol, which differs from hydroxymatairesinol in that R3 denotes group =O, didemethyl matairesinol, which differs from hydroxymatairesinol in that R4 and R3 denote hydrogen, isohydroxymatairesinol, alpha-conidendrin (R1 denotes group =O, R2 denotes the oxygen atom pertaining to the hetero ring C, R4=$CH_3$, R7=$OCH_3$, R8=OH, R6=H, R3 is a bond to the carbon 6, R9=H), alpha-conidendric acid (R4=$CH_3$, R7=$OCH_3$, R5=R8=OH, R6 denotes group =O, R1=R2=OH, R3 is a bond to the carbon 6, so that the carbons 6, 1, 7, 8, 8', 7' form a cyclohexane ring D that is condensed with the phenyl ring A, R9=H), liovile (R4=$CH_3$, R7=$OCH_3$, R3=R5=R6=R8=OH, R1=H, R2 denotes the oxygen atom pertaining to the hetero ring C, R3 denotes a bond to the carbon 6, R9=H), secoisolariciresinol (R1=R2=OH, R3=H, R4=$CH_3$, R7=$OCH_3$, R5=R8=OH, R6=R9=H), dimethyl secoisolariciresinol, which differs from secoisolariciresinol in that R5 and R8 are methoxies, isolariciresinol (R1=R2=OH, R4=$CH_3$, R7=$OCH_3$, R5=R8=OH, R6=H, R3 is a bond to the carbon 6, so that the carbons 6, 1, 7, 8, 8', 7' form a cyclohexane ring D, which is condensed with the phenyl ring A, R9=H), cyclolariciresinol (R1=R2=OH, R3=a bond to the carbon 6, so that the carbons 6, 1, 7, 8, 8', 7' form a cyclohexane ring D, which is condensed with the phenyl ring A, H, R4=$CH_3$, R7=$OCH_3$, R5=R8=OH, R6=R9=H), nortrachelogenin (R1 denotes group =O, R2 denotes the oxygen atom pertaining to the hetero ring C, R3=R6=H, R4=$CH_3$, R7=$OCH_3$, R5=R8=OH, R9=OH), In Formula IB:
R10 denotes hydrogen or hydroxy
R11 denotes hydroxy or oxygen, which is bound by a bond to the carbons 7 and 9', forming now an oxygenous non-aromatic 5-membered heterocyclic ring (tetrahydrofuran) F with the carbons 7, 8, 8', 9', which ring is condensed in the hetero ring E (tetrahydrofuran) at the carbons 8, 8',
R12 denotes hydrogen or methyl,
R13 denotes hydrogen or methoxy,
R14 denotes hydrogen or methoxy,
R30 denotes hydrogen or group =O.

Advantageous compounds according to formula IB are: pinoresinol (R13=R14=R12=R10=R30=H, and R11 is oxygen in the hetero ring F); isohydroxymatairesinol (R12=R13=R14=R10=H, R11=OH, R30 denotes group =O); lariciresinol (R12=R13=R14=R10=R30=H, R11=OH); and lignan A (R10=R11=OH, R12=R13=R14=R30=H).

Stilbenes in turn refer to compounds according to the general formula II (Appendix),
where R15 denotes hydrogen or hydroxy
R16 denotes residue selected from the groups H, OH, OCH₃,
R17 denotes residue selected from the groups OH or OCH₃,
R18 and R19 denote, irrespective of each other, hydrogen or hydroxy,
R20 denotes residue selected from the groups hydrogen, OGlu A few advantageous stilbenes according to formula II are pinosylvin (R18=R19=R20=R15=H, R16=R17=OH), monomethyl ether of pinosylvin (R18=R19=R20=R15=H, R16=OCH₃, R17=OH), dihydropinosylvin (R18=R19=R20=R15=H, R16=R17=OH, the phenyl elements bonding ethenyl residue is hydrated to ethyl), resveratrol (R16=R17=R19=OH, R18=R20=H), astringin (R15=R17=OH, R16=R19=H, R18=OH, R20=OGlu and isorhapontine (R16=R19=H, R17=OCH₃, R15, R18=OH, R20=OGlu).

Juvabiones refer to compounds according to formula III (Appendix).

Flavonoids refer to compounds according to general formula IV (Appendix), where
R21 denotes residue selected from the groups H, OH,
R22 denotes residue selected from the groups H, OH, =O,
R23 denotes residue selected from the groups H, OH
R24, R25, R26 denote, irrespective of each other, hydrogen or hydroxy,
R26 and R27 denote, irrespective of each other, hydrogen or hydroxy.

Among advantageous compounds according to formula IV are dihydromyricetin (R27=H, R21=R23=R24=R25=R26=R28=OH, R22 is oxo group), taxifolin (R24=R27=H, R21=R23=R25=R26=R28=OH, R22 is oxo group), dihydrokaempferol (R24=R26=R27=H, R21=R23=R25=R28=OH, R22 is oxo group), catechin (R24=R26=R27=H, R21=R23=R25=R26=R28=OH, R22 is hydrogen), naringenin (R23=R24=R26=R27=H, R21=R25=R28=OH, R22 is oxo group), kaempferol (R24=R26=R27=H, R21=R23=R25=R28=OH, R22 is oxo group), teracasidine (R21=R=24H, R22=R23=R25=R26=R27=R28=OH, ketoteracasidine (R21=R24=R26=H, R23=R25=R27=R28=OH, R22 is oxo group), isoteracasidine (R21=R24=R26=H, R22=R23=R25=R27=R28=OH), melacasidine (R21=R24=H, R22=R23=R25=R26=R27=R28=OH), isomelacasidine (R21=R24=H, R22=R23=R25=R26=R27=R28=OH), pinobanxin (R24=R25=R26=R27=H, R21=R23=R28=OH, R22 is oxo group) and pinosembrin (R23=R24=R25=R26=R27=OH, R21=R28=OH, R22 is oxo group).

Betulin, by systematic name (IUPAC) lup-20(29)-ene-3β, 28-diol, and its derivatives refer to compounds according to formula 1E. In the formula 1E, betulonic acid is compound 2, and betulinic acid is compound 3. Betulin is compound 1. Compounds 2 and 3 are obtained by oxidizing betulin 1 into compound 2, and by reducing compound 2 into compound 3 (U.S. Pat. No. 6,280,778). Betuloinic acid is a

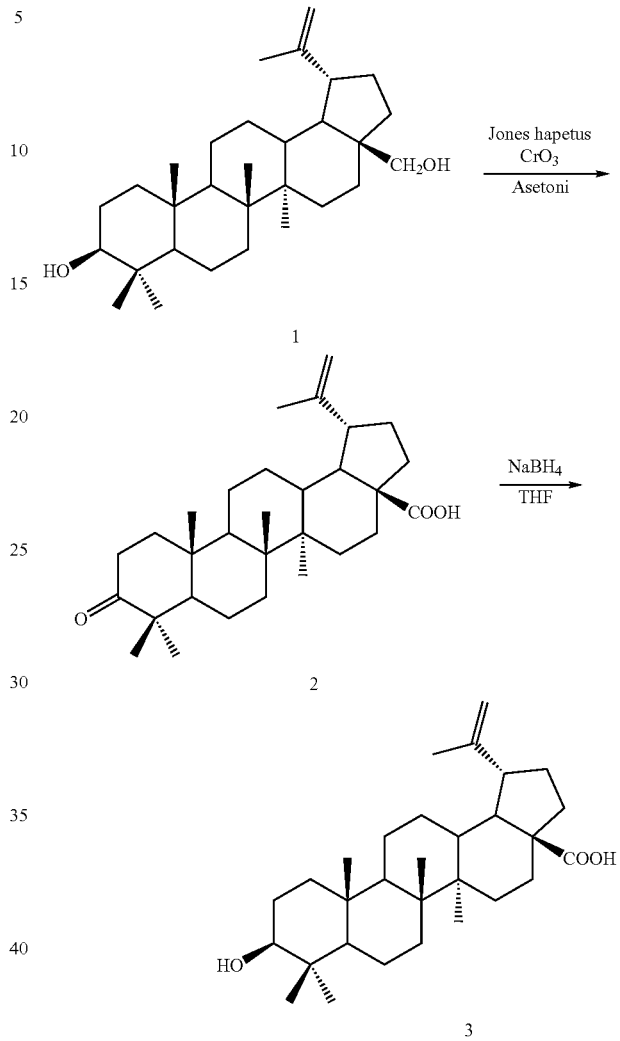

derivative of betulonic acid.

Exemplary oligolignans are beta bound guaiacyl ethers of lignans and stilbenes (trimeric so-called sesquilignans) and coumarates such as secoisolariciresinol guaiacyl glycerol ether, nortrachelogenin guaiacyl glycerol ether, hydroxymatairesinol guaiacyl glycerol ether, lariciresinol guaiacyl glycerol ether, liovile guaiacyl glycerol ethers, conidendrin guaiacyl glycerol ether, pinoresinol guaiacyl glycerol ether, lariciresinol coumarate and secoisolariciresinol coumarate (Willför et al, Holzforchnung, Vol 58, 3435-354, 2004) and dilignans such as 5-5-bis-secoisolariciresinol, 5-5-bis-isolariciresinol, 5-5-bis-lariciresinol.

Depending on the pH, phenolic compounds occur in the compositions either as free, esterized or etherized forms, wherefore also said ester and ether derivatives belong within the scope of the invention.

The phenolic compounds contained by the compound mixture according to the invention are well tolerated by mammals, they have a low cytotoxicity and they neither spontaneously form nor induce free radicals. In a field test, we have compared the cytotoxicity of the polyphenolic mixture according to the invention with the cytotoxicity of an antioxidant butylated hydroxytoluene (BHT) that is widely used in the food and cosmetic industry.

Thus, most of the compound mixtures according to the invention are relatively mild antimicrobial agents, but this is compensated in that owing to their non-toxic nature, they can be used in remarkably higher quantities.

One of the most important properties of the compound mixtures according to the invention is their minimal penetration to skin, wherefore skin irritation does not occur when using them, as opposite to the conventionally used antimicrobial compounds. The applicant has studied the skin irritation of the compound mixtures according to the invention in a so-called single patch test and found out that they do not irritate the skin with 0.1 wt % contents, and not even with 1 wt % contents; often even 5 wt % contents can be used without excessive skin irritation.

The low cytotoxicity of the compound mixtures according to the invention, as combined to a minimal skin irritation, ensures that the compound mixture according to the invention can be used in sufficiently large quantities, particularly in cosmetic compositions. Thus, by using the compound mixtures, the antimicrobial effect of the agent used as the first antimicrobial agent can be expanded or increased, and at the same time the cytotoxicity of the effective agents as well as their skin irritation can be maintained sufficiently low.

One of the most important properties in compositions provided with a compound mixture according to the invention is that the compound mixture of phenolic compounds present in the compositions inhibits on a wide scale the growth of antimicrobial agents, when it is added in the composition for 0.1-5 wt %. Generally the amount of synthetic widely antimicrobial agents that can be added to compositions is only roughly 0.01-0.03 wt %, owing to their high cytotoxicity, in case the compositions get into contact with mammal skin at some stage of their usage life. As for Gram-negative bacteria, a mixture of phenolic compounds has a growth inhibiting effect at least against $E.$ $coli,$ $Ps.$ $aeruginosa,$ $Ps.$ $putida,$ and $Kl.$ $pneimoniae;$ as for Gram-positive bacteria, it has a growth-inhibiting effect at least against $S.$ $aureus;$ as for yeasts, it has a growth-inhibiting effect at least against $M.$ $furfur$ and $C.$ $albicans,$ and as for fungi, a growth-inhibiting effect at least against $A.$ $niger.$ A particularly surprising feature in the invention is that although it has been found out that several pure lignan, stilbene or flavonoid compounds, or knot extracts obtained from trees containing abundantly such lignans, stilbenes or flavonoids, have a limited effect against the growth of microorganisms, yeasts or fungi, it has not been verified that they should have a wide-scale antimicrobial effect, and they have not been found effective for example against certain important Gram-positive bacteria such as $S.$ $aureus$ (cf. e.g. Välimaa et al., International J. of Microbiology, 115 (2007) 235-243). Moreover, it has earlier been shown that stilbene-bearing raw extracts and solutions containing refined stilbenes are relatively cytotoxic (e.g. International J. Food Microbiology, 115 (2007) 235-243), which does not encourage a man skilled in the art to use these extracts in cosmetic products.

The wide-scale antimicrobial effect of the compound mixtures containing phenolic compounds used in the invention, combined with their low cytotoxicity, is a surprising feature, because in the raw extracts obtained from knotty knotwood described in the prior art, their antimicrobial effect has not been verified as particularly wide-scale, not even for raw extracts containing stilbenes.

By using the microbial growth inhibiting compound mixture according to the invention, it is often possible to modify the harmful properties of other antimicrobial agents, such as microbicidic and bacteriostatic agents contained in the composition, by trapping the free radicals created during their decomposition, which reduces the cytotoxicity and skin irritation of these agents.

A new feature with compositions realized by means of compound mixtures is their improved in vivo sun protection factor SFP, in comparison with measurements in vitro.

By adding the compound mixture according to the invention to cosmetic and food industry compositions, with an antioxidant such as a vitamin present as the first effective agent, the effective profile of antioxidants, as well as their effective time, can be adjusted, and their cytotoxicity reduced.

Yet another way to use the compound mixtures according to the invention is to add them to the coating of finely divided inorganic UV protection agents. In that case the compound mixture has free radical neutralizing effects, which is an effective way to prevent the unwanted effects of free radicals created of the inorganic UV protection agent, such as the skin irritation caused by them.

Among others, the antimicrobial compound mixture according to the invention can be used in cosmetic compositions and their semifinished compositions, such as sun protection compositions and in semifinished products used in the manufacturing of sun protection compositions. The compound mixture can also be used in so-called commercial solvents, such as surface treatment agents, solvents used in the cleaning branch solvents etc.

DESCRIPTION OF PREFERRED EMBODIMENTS OF THE INVENTION

The compound mixture according to the invention can advantageously be used in sun protection compositions and in semifinished products used in the manufacturing of sun protection compositions.

As was already pointed out, the organic UV protection agents used in sun protection compositions may themselves induce the creation of free radicals, in the topmost layer of the sun protection composition applied on the skin is worn off, or in case the UV protection agents have access to be absorbed in the skin, and a new layer of sun protection composition is not applied on the skin. Organic UV protection agents function either by absorbing UV radiation and by transforming it to a longer-wave radiation that is less harmful to skin cells (for example into heat), or then they capture the free radicals created on the skin owing to the effect of the UV radiation. The compound mixtures according to the invention, containing phenolic compounds, have free radical capturing properties, wherefore they can be used for inhibiting the creation of free radicals from organic UV protection agents, when they are exposed to UV radiation. By adding a compound mixture according to the invention, containing (poly)phenolic compounds, in sun protection compositions containing organic UV protection agents, or in semifinished products used in the manufacturing thereof, containing organic UV protection agents, it is possible to prevent the organic UV protection agents from themselves turning cytotoxic to the system. A mixture according to the invention, containing phenolic compounds, also has UV radiation absorbing properties itself, the compound mixture does not spontaneously create reactive free radicals, and the manufacturing expenses of the compound mixture are low and availability good, wherefore it can advantageously be used for replacing part of the expensive organic UV protection agents. The effective mechanism of the polyphenols contained in the compound mixture according to the invention would appear to be mainly based on that the phenolic compounds contained in the compound mixture go through an automatic oxidation-reduction reaction after neutralizing the free radicals. This automatic oxidation-reduction reaction ends in the formation of stabile dimers. A secondary effect of the compound mixture according to the invention is in that they are capable of absorbing UV radiation and of preventing the action of free radical creating enzymes, and/or of preventing the action of metal ions catalyzing the creation of free radicals or of decomposing hyperoxides. Mixtures according to the invention can be used, among others, with the following protection agents in sun protection compositions or in semifinished products used in the manufacturing of sun protection compositions:

Avobenzon (BMDN i.e. 1-(4-methoxyphenyl)-3-(4-tert.-butylphenyl)propane-1,3-dione, octyldimethyl-4-aminobenzoic acid. Avobenzon absorbs UVA radiation in a wide spectrum. Avobenzon is often used in sun protection compositions together with titanium oxide in order to expand the effective spectrum thereof. Because Avobenzon is gradually decomposed owing to the effect of sunlight, various photostabilizers are often used for stabilizing it, among them Octocrylene, as well as triazine derivatives (bis-ethylhexyl oxyphenyl triazine or methylene-bis-benzotriazolyl) known by the trade names Tinosorb® S and Tinosorb® M, which also are UV protection agents;

octyldimethyl, 4-aminobenzoic acid (para-aminobenzoic acid i.e. PABA);

octyl methoxy cinnamate (OMC) i.e. 3-(4-methoxyphenyl)-2-propenoic acid 2-ethylhexyl ester;

benzophenon-3 i.e. 2-hydroxy-4-methoxyphenyl-phenyl methanon;

octocrylene;

as well as MBBT, i.e. methylene-bis-benzotriazolyl tetramethyl butyl phenol

Other known compounds used as UVA and UVB protection agents that can be applied in the compositions according to the invention are, among others, EHMC (ethylhexyl methoxycinnamate, BNBM (ethyl hexyl methoxy dibenzoyle methane), BMC (4-methyl bentzylidene camphor), BP3 (3-benzophenone), DTS (drometrizole trisiloxane), DPDT (disodium phenyl dibenzimidazole tetrasulphonate), BEMT (bis-ethyl oxyphenol methoxyphenyl triazine), IMC (isoamyl p-methoxycinnamate), PBSA (phenyl benzimidazole sulphonic acid), OT (octyl trazone), OS (octyl salicylate), TDSA (terephthalidene dicamphor sulphonic acid) and the physical and organic compounds accepted by EU and FDA as UV protectors, as well as the compounds enlisted in the INCI list, with respect to which we refer to the known literature on the field.

The effective agents contained in the composition, for example organic UV protection agents meant for a sun protection composition, are efficiently prevented from themselves turning into free radical inducing agents or even free radicals, by adding into the composition a compound mixture that inhibits the formation of said free radicals or is capable of trapping the created free radicals. When the purpose of the compound mixture is to prevent the UV protection agents from creating skin irritating free radicals, or when the purpose of the compound mixture is to prevent said UV protection agents from inducing the creation of free radicals in the conditions of usage of the composition, there is used a compound mixture according to the invention, by which the in vivo protective factor of the UV protection agent can be adjusted, even if its protective factor measured in vitro conditions remains the same.

In sun protection compositions manufactured according to the invention, there can also be used inorganic (mineral) UV protection agents, such as finely divided $TiO_2$ or $ZnO$, $Fe_xO_y$, and $CeO_2$, alone or together with organic UV protection agents. As was already pointed out above, these inorganic UV protection agents must be coated with a suitable protective layer, such as an aluminum oxide layer, and also dispersed in a suitable medium for preventing aggregation. In the coating of inorganic finely divided UV protection agents, there can possibly be included a mixture according to the invention, which mixture contains, as polyphenolic compounds, lignans, stilbenes, juvabions and/or flavonoids as well as their oligomers, preferably lignans and their oligomers. This kind of mixture according to the invention, extracted from a suitable raw material source, has free radical neutralizing effects, by which any undesirable effects of the free radicals created from inorganic UV protection agent are efficiently eliminated. The phenolic compounds of the compound mixture, including conjugated carbonyl groups, neutralize a free radical possibly formed of the inorganic protective agent (for example $TiO_2$) by giving up electrons to the created reactive radical, and by at the same time forming dimers. Moreover, the compound mixture prevents the functioning of the inorganic UV protection agent as a catalyst in aqueous conditions, where it could otherwise induce the creation of free radicals.

The compound mixture also has same properties as the UV protection agent (the compound mixture absorbs UV radiation and captures free radicals induced on the skin owing to the effect of UV radiation), and therefore it can also be used for boosting the protective effect against UV radiation of the inorganic UV protection agent in the composition in vivo, when the UV protective factor of the composition in vitro remains roughly the same, and/or for adjusting the protection profile of the UV protection agent in different UV ranges. By replacing part of the inorganic UV protection agent by a polyphenolic compounds containing mixture according to the invention, with economical manufacturing expenses and a good availability, the composition manufacturing expenses can be maintained the same or even reduced.

The inherent melanin of the skin, appearing a few days after exposure to UVA radiation, as stimulated by the alpha-melanocyte hormone, inhibits UV radiation from penetrating deeper in the skin layers by trapping the free radicals induced on the skin. In compositions according to the invention, there can be used UV protection agents with a UV radiation protective effect similar to that of melanin. One such UV protection agent with a melanin-like effect is a UV protection agent composition, composed of several inorganic UV protection agents and used as a semifinished product in color cosmetic compositions. This semifinished product contains extremely fine $TiO_2$ particles, $TiO_2$ pigment and iron oxides. These inorganic UV protection agents are coated, for instance as was described above, by a suitable coating layer. In this coating layer, there is included a phenolic compound mixture according to the invention, which both inhibits said inorganic UV protection agents from themselves inducing free oxygen containing radicals on the user's skin, and which mixture also has properties for protecting the skin against UV radiation.

The free radical capture rate of polyphenolic compounds present in a compound mixture according to the invention differs from said rate in general sun protection compositions, among others, and from the rate in synthetic antioxidants BHT and BHA used as antioxidants in foodstuffs. Synthetic antioxidants, such as the above mentioned BHT and BHA, are generally cytotoxic, which means that their use as antioxidants is restricted. Moreover, the reaction speed of synthetic antioxidants also is fairly slow, and they only function in certain limited reaction conditions. On the other hand, a polyphenolic compounds containing mixture according to the invention has a remarkably low rate of cytotoxicity, when measured as the susceptibility of the compound mixture to create free radicals itself, and in addition to this, the free oxygenous radicals capturing capacity of the compound mixture per unit of time and unit of weight is different than with BHT and/or BHA. Because the compound mixture according to the invention has antioxidative effects, it can be used for replacing part of the share of BHT and BHA that have been found cytotoxicity, for instance in foodstuffs and sun protection compositions, or in semifinished products of sun protection compositions containing BHT or BHA. As an alternative, the compound mixture according to the invention can be used for ensuring a sufficient quantity of antioxidants in a composition that already contains the maximum allowed quantity of BHA or BHT, because these cannot be added in foodstuffs, owing to their cytotoxicity, more than their permitted share.

The problem with the use of both synthetic and natural antioxidants is either their slow reaction speed or their extremely selective way of functioning, i.e. they only inhibit certain oxidation reactions (synthetic antioxidants), or their thermolabile nature and their susceptibility to decomposition caused by UV light (natural antioxidants, vitamins). The reaction speed of a compound mixture according to the invention is remarkably higher than that of synthetic mixtures, and they are not especially selective but inhibit a wide range of oxidation reactions and react, among free radicals, for example with peroxide radicals, lipid radicals, superoxide-anion and peroxidase radicals. The UV light resistance of compound mixtures according to the invention is good, and they are thermally stabile.

The compound mixture according to the invention can also be used for technical purposes in various solvents, in liquids used in the machining of metals with chip removal, in cleaning liquids, liquid surface treatment agents, wood preparation fluids, drilling fluids etc. During usage, these liquids may get into contact with human skin, and in that case the microbicidic and bacteriostatic compounds contained therein may cause various allergic reactions and skin damages. In these technical solutions, the phenolic compound mixture according to the invention can be used for partly replacing for example the skin irritative microbicides contained by said solutions, or antimicrobial agents; the compound mixture according to the invention has antimicrobial effects, but it does not, however, irritate the skin as much as the synthetic antimicrobial agents.

The phenolic compound mixture according to the invention is produced either by pulverizing or by extracting wood material, or by combining said procedures. Because the wood material most widely available in Finland is pine or spruce, of which particularly the latter contains resin, the extraction is generally realized in two steps. Now resin compounds are extracted from the pulverized pine material, advantageously pulverized knotwood or stem knotwood material, by a lipophilic extraction solvent, and successively the polyphenols are extracted by a hydrophilic extraction solution. The lipophilic organic extraction solution is for example hydrocarbon, such as lower alkane, for example hexane or heptane. Generally the hydrophilic organic extraction solution is an organic compound containing a carbonyl group, such as alcohol or ketone. Ketone can be used only in case the compound mixture is meant for technical usage. An advantageous ketone is a lower alkyl ketone such as acetone. In case the compound mixture to be produced is a compound mixture in pulverized form, water is removed from the pulverized stemwood knot material by freeze-drying.

Advantageously the alcohol is a monovalent, bivalent or trivalent lower alkyl alcohol, or a mixture of these. The monovalent lower alkyl is preferably ethanol, propanol, butanol, heptanol, octanol or decanol. A mixture of a lower alkyl alcohol and glycerol or glycol is an advantageous solvent agent when producing several skin care compositions or semifinished products of skin care compositions. As for the lower alkylene glycol used as the hydrophilic extraction solution, it is preferably selected from a group comprising propylene glycol, butylene glycol, pentylene glycol and dipropylene glycol. Of these, the latter is particularly advantageous to be used in perfumes. In this kind of extract solution or in an extract concentrate obtained therefrom, the content of alkylene glycol is more than 70 wt %, preferably more than 90 wt %.

Extraction of Phenolic Compounds from Wood Material and the Properties of the Extracted Phenolic Compounds The composition of a compound mixture containing phenolic compounds, obtained from one and the same wood material by different extraction methods, fluctuates to some extent. The extraction method is selected according to the target of usage of the composition (for instance use in commercial solvents or cosmetic compositions), and according to the desired properties of the compound mixture. For example from Table 1 to be described below, it can be observed that the total quantities of polyphenolic lignan and stilbene compounds contained in pine knotwood and obtained by various extraction methods, as well as the mutual ratios of said polyphenolic compounds, fluctuated to some extent. Moreover, the obtained extract contained a certain amount of resin elements.

TABLE 1

Table 1 illustrates extracts obtained by different extraction methods from pulverized knotwood material of pine stem (scots pine).

| Compound | Test 1 % of peak | Test 2 % of peak | Test 3 % of peak | Test 4 % of peak |
| --- | --- | --- | --- | --- |
| PSMME | 16 | 17 | 23 (14) | 29 (16) |
| PS | 15 | 20 | 19 (12) | 20 (12) |
| NTG | 16 | 30 | 30 (18) | 33 (19) |
| Resin acids | 18 | 16 | 12 (7) | 10 (6) |
| Oxidized resin acids | 35 | 17 | 17 (10) | 8 (5) |

In all tests 1-4, there were extracted pine chips composed of stem knotwood. These were first extracted with hexane; in test 4, a technical hexane was used. After the extraction of lipophilic hexane, the samples were extracted with various hydrophilic solutions: in test 1 with acetone, in test 2 with ethanol (96%), in test 3 with acetone and in test 4 again with 96% ethanol. In tests 1 and 4, there were used chips which were mixture of dead and live wood material; in tests 2 and 3, the employed wood material consisted of hand-picked dead stem knotwood chips. After extraction, the quantities of the phenolic and resin compounds contained by the samples were analyzed by liquid-gas-chromatography. The contents of various compounds are given as a percentual area of the peak shown by each compound in relation to the area of all peaks. In tests 3 and 4, the weights of different compounds are given in parentheses with respect to the total weight of the solution.

Abbreviations of the compounds in the Table: PSMME: pinosylvin monomethyl ether (stilbene); PS: pinosylvin (stilbene); NTG: nortrachelogenin (lignan).

It has been discovered that raw extracts from pine knotwood are both microbial growth inhibiting on a wide scale, and also anti-inflammatory, obviously owing to the stilbene compounds contained therein, such as pinosylvin and its derivatives. Thus for example knot extracts containing unpurified phenolic compounds according to Table 1, from tests 1 and 3, can be used as such in commercial solvents. The pine knot extract obtained from examples 2 and 4, could in turn be used as such as a semifinished product for manufacturing various cosmetic compositions, without further purifying, in case the antimicrobial compounds used in said products should be replaced by a mixture containing physiologically better tolerated phenolic compounds.

It has been found out that an unpurified knot extract solution obtained from spruce stem knotwood material by hydrophilic extraction has, in its spectrum of influence, a similar wide-scale microbial growth-inhibiting effect as knot extracts obtained from pine stem knotwood. A raw extract extracted from spruce knotwood in alcohol contains mainly lignans and oligolignans (cf. Table 2A below). Lignans contain mainly hydroxymatairesinol, secoisolariciresinol, conidendrin and oligolignans, as well as smaller amounts of other lignans such as liovile and lariciresinol. Although the microbial growth inhibiting effect of polyphenolic lignan compounds contained in a raw extract obtained from spruce stem knotwood by alcohol is weaker than with raw extracts obtained from pine stem knotwood, said extracts obtained from spruce stemwood chips by hydrophilic extraction can be used for producing cosmetic compositions according to the invention and their semifinished products owing to their low cytotoxic effect and low skin irritation.

TABLE 2A

Polyphenolic compounds contained in a solution extracted from Norway spruce stemknot wood by pentylene glycol, as defined by a gas-liquid chromatography. The raw knot wood extract contained 87-93 wt % pentylene glycol (solvent) and 6.5-7.5 wt % polyphenolic compounds (mainly lignans) extracted from spruce.

| | |
|---|---|
| Hydroxymatairesinol | 70-80% |
| Secoisolariciresinol | 3-6% |
| Conidendrin | 4-7% |
| Lariciresinol | 1-3% |
| Liovile | 2-5% |
| Other lignans | 5-8% |

As is seen from Table 2A, spruce contains mainly lignans, of which the majority is hydroxymatairesinol. The other lignans mentioned in the Table 2A are mainly oligolignans. A raw knot wood extract obtained from spruce knotwood in alcohol contains mainly lignans and oligolignans (cf. table 2A above).

In case the extraction methods are changed, lignans can be transformed to other lignans. For example, 7-hydroxymatairesinol can in alkaline extraction conditions be transformed to alpha-conidenrin and further to alpha-conidendric acid or 7-hydroxymatairesinolic acid, and further to isohydroxymatairesinol. In acidic extraction conditions, 7-hydroxymatairesinol is transformed to isohydroxymatairesinol, and alpha-conidendric acid in turn is transformed to cyclolariciresinol, and secoisolariciresinol is in acidic conditions transformed to anhydrosecoisolariciresinol.

Unpurified extracts obtained from pine stemknot wood by hydrophilic extraction contain a remarkable quantity of stilbene compounds. The applicant has verified that these extracts inhibit the growth of micro-organisms (Gram-positive and negative bacteria, fungi and yeasts) in a wide scale. Thus, pine is a good source of the antimicrobial compound mixtures according to the invention. It has also been discovered that stilbenes have anti-inflammatory properties. On the other hand, unpurified raw extracts obtained from spruce knotwood contain mainly lignans; the applicant has verified that said lignans have, by their spectrum of influence, a similar but weaker effect for inhibiting the growth of micro-organisms than stilbene-bearing raw extracts obtained from pine. Both raw extracts extracted from pine stem knotwood and containing mainly stilbenes, as well as raw extracts extracted from spruce stem knotwood and containing mainly lignans, are feasible when manufacturing different compositions that have an antimicrobial effect and at the same time low skin irritation and low cytotoxicity in comparison with BHT.

From the pulping processes of wood processing industry, there is obtained remarkably more spruce than pine, which fact is in favor of a solution that the compound mixtures according to the invention comprise compound mixtures of unpurified extraction solutions obtained from spruce by hydrophilic extraction, or unpurified extraction solutions obtained from spruce and pine by hydrophilic extraction. In a suitable arrangement, the combined extraction solutions according to the invention contain for example 70 wt % (poly)phenolic compounds (lignans and oligolignans) extracted from spruce stem knotwood, and 30 wt % (poly) phenolic compounds extracted from pine stem knotwood, with stilbenes included. Other mixture ratios can also be applied, as long as attention is paid to the fact that the compound mixture contained in the combined extraction solution obtained from pine and spruce has a sufficiently low cytotoxicity (the employed reference is BHT).

The applicant has discovered that when the mutual mixing ratios of the raw extracts obtained from different wood species are selected so that the cytotoxicity for the powdered or extracted compound mixture, expressed as wt % from total content of the end composition, when measured in ethanol for a HaCat cell culture after 24 incubations, is lower than the cytotoxicity of 0.02-0.1 wt % BHT % from total content of the end composition dissolved in ethanol in the same incubation conditions, preferably lower than the cytotoxicity of 0.01-0.05 wt % BHT % from total content of the end composition dissolved in ethanol in the same incubation conditions, the allowed quantity for the employed mixture is 0.1-5 wt % of the total weight of the end composition, in most cases 1-5 wt % of the total weight of the end composition. This limit value of the content is remarkably higher than with most commercially available wide-scale, microbial growth inhibiting synthetic substances, which means that the compound mixtures according to the invention can be used in sufficient quantities for ensuring their wide-scale antimicrobial effect.

Hardwood species contain remarkable quantities of different flavonoids, biflavonoids and flavonoid glycosides, as is apparent from Table 2B below. Unpurified raw extracts containing flavonoids, obtained from hardwood species, have antioxidative and free radical capturing properties, wherefore they can be used for example together with raw extracts obtained from pine or spruce stem knotwood for producing compound mixtures containing phenolic compounds according to the invention, as well as their intermediate products.

Mixtures according to the invention can be isolated from wood material in general. An advantageous raw material source consists of wood branches and stem's knotwood parts, but also other wood parts, such as stemwood, wood bark and needles can be used.

TABLE 2B

The principal components of unpurified extraction solutions obtained by hydrophilic extraction from stem knotwood of various hardwood species.

| *Acacia crassicarpa* | |
|---|---|
| Flavonoids | 54% |
| Melacasidine | 24% |
| Isomelacasidine | 18% |
| Biflavonoids | 9% |
| *Acacia mangium* | |
| Flavonoids | 36% |
| Teracasidine | 25% |
| Ketoteracasidine | 3% |
| Biflavonoids | 8% |
| *Fagus sylvatica* | |
| Flavonoids | 7% |
| Catechin | 6% |
| *Eucalyptus globulus* | |
| Tannins | 19% |
| Tannin monemers | 5% |
| Ellagic acid | 3% |
| Gallic acid | 2% |
| *Populus grandidentata* | |
| Flavonoids | 31% |
| Dihydrokaempferol | 13% |
| Catechin | 9% |
| Naringenin | 7% |
| Taxifolin | 3% |
| Flavonoid glycosides | 34% |
| *Populus tremula* | |
| Flavonoids | 21% |
| Dihydrokaempferol | 17% |
| Naringenin | 3% |
| Flavonoids glycosides | 8% |
| *Populus tremuloides* | |
| Flavonoids | 23% |
| Dihydrokaempferol | 17% |
| Naringenin | 10% |
| Kaempferol | 1% |
| Taxifolin | 1% |
| Flavonoid glycosides | 24% |

Compounds isolated from birch bark are enlisted in Table 3A below and FIG. 1 illustrates compounds isolated from birch bark.

As can be observed for example from Table 3A, extracts obtained from the bark of different wood species by hydrophilic extraction contain various polyphenolic flavonoid compounds. In the present invention, these unrefined extracts mainly containing flavonoids can be used either as such or preferably together with hydrophilic extracts obtained from other the material of wood species, to be further used for producing various compositions according to the invention and their semi-finished products. One source of these advantageous flavonoids is the bark of birch (*Pendula betula*).

TABLE 3A

Principal components of unpurified extraction solutions obtained from the bark of different wood species by hydrophilic extraction (Extractives in stemwood and knots of Acasia and Aspen trees, Suvi Pietarinen, Abo Akademi, Turku 2005).

| *Thuja occidentalis* |
|---|
| Sugars |
| Catechin |
| Isorhapontine |
| Astringin |
| Tannins |
| *Pinus banksiana* |
| Sugars |
| Taxifolin |
| Isorhapontine |
| Dihydromyrcetin |
| Tannins |
| *Betula pendula* |
| Betuligenili glycoside |
| Catechin |
| Sugars |
| Tannins |
| *Pseudotsuga menziensii* |
| Sugars |
| Taxifolin |
| Catechin |
| Tannins |
| *Picea abies* |
| Isorhapontine |
| Astringin |
| Resvatrol-glycoside |
| Tannins |
| *Abies lasiocarpa* |
| Sugars |
| Resin acids |
| Tannins |
| *Populus tremula* |
| Undefined glycosides |
| Tannins |
| *Pinus mariana* |
| Sugars |
| Catechin |
| Tannins |

FIG. 1

Cycloisolariciresinol

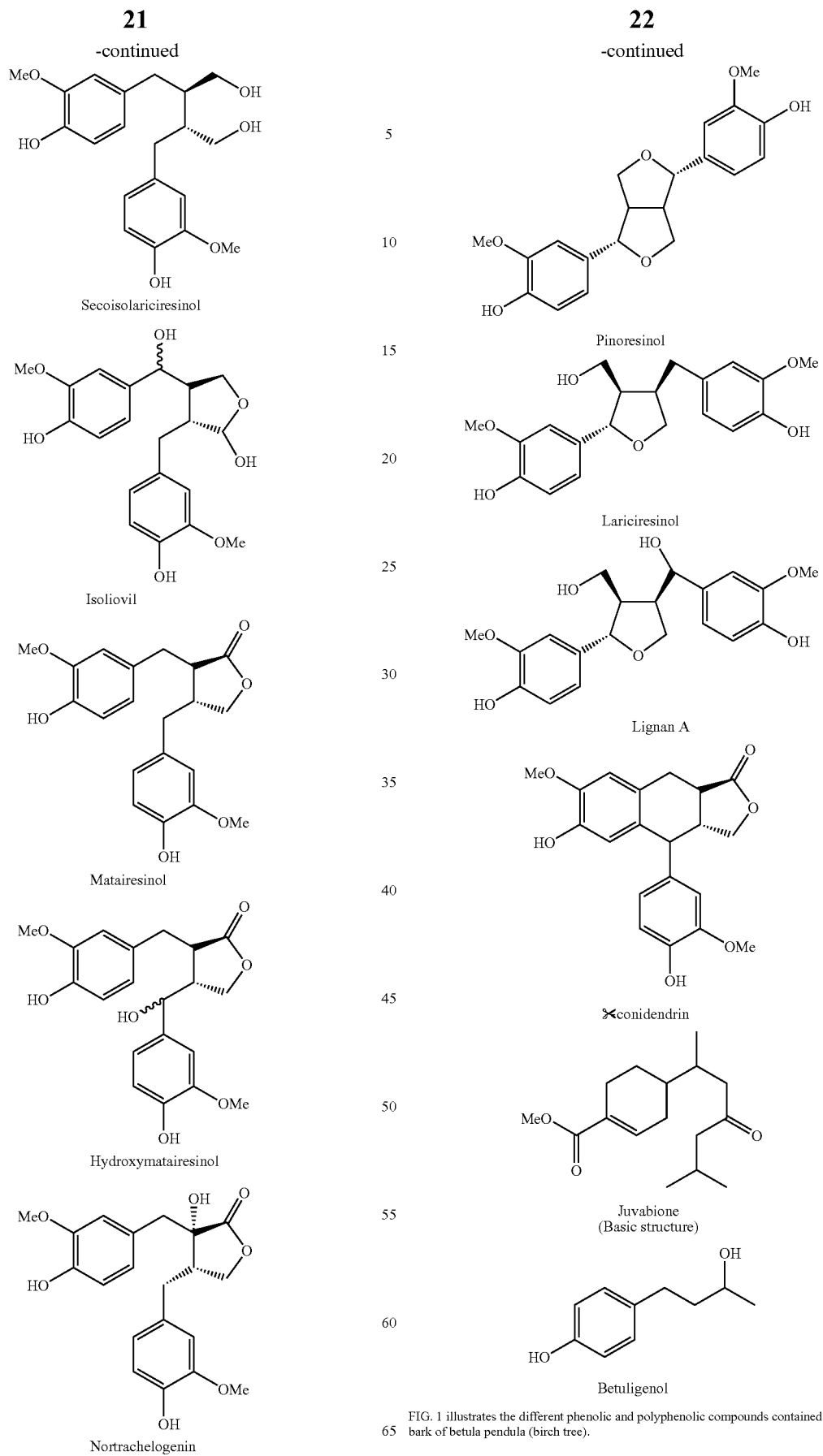
FIG. 1 illustrates the different phenolic and polyphenolic compounds contained in the bark of betula pendula (birch tree).

As can be observed from FIG. 1, also birch bark contains lignans, stilbenes, flavonoids and juvabiones as polyphenolic compounds, wherefore it can also be used as a raw material for producing a compound mixture according to the invention. Phenolic betuligenol, mentioned at the end of FIG. 1, as well as its derivatives betulinic acid, betuloinic acid or betulonic acid, can also be used in compound mixtures according to the invention, either as separately added therein in separately purified form, or together with an unpurified compound mixture obtained from birch bark extraction.

TABLE 3B

Principal components of unpurified extracts obtained from the stem knotwood of a few pine and spruce species by hydrophilic extraction (Wilför et al., J. Agric. Food. Chem., 51, 26 (2003)), in percentages by weight of the total quantity of the components of the compound mixture extracted from the wood.

| Wood material | Compounds | wt % |
|---|---|---|
| *Picea abies* | | |
| | Lignans | 53 |
| hydroxymatairesinol | | 41 |
| secoisolariciresinol | | 3 |
| α-conidendrin | | 7 |
| Oligolignans | | 12 |
| *Abies sibirica* | | |
| Lignans | | 33 |
| secoisolariciresinol | | 21 |
| lariciresinol | | 7 |
| Oligolignans | | 31 |
| Juvabiones | | 3 |
| *Abies balsamea* | | |
| | Lignans | 22 |
| secoisolariciresinol | | 18 |
| lariciresinol | | 9 |
| | Oligolignans | 19 |
| | Juvabiones | 2 |
| *Pinus sibirica* | | |
| | Lignans | 26 |
| lariciresinol | | 19 |
| isolariciresinol | | 3 |
| secolariciresinol | | 2 |
| Oligolignans | | 6 |
| | Flavonoids | 7 |
| pinosembrin | | 6 |
| | Stilbenes | 25 |
| dihydropinosylvin monomethyl ether | | 15 |
| pinosylvin | | 3 |
| dihydropinosylvin | | 2 |
| *Pinus contorta* | | |
| | Lignans | 10 |
| nortrachelogenin | | 5 |
| liovile | | 3 |
| oligomers | | 3 |
| | Flavonoids | 20 |
| pinosembrin | | 15 |
| pinobanxin | | 7 |
| | Stilbenes | 15 |
| Pinosylvin monomethyl ether | | 9 |
| Pinosylvin | | 6 |

In FIG. 2 below is introduced polyphenolic compounds present in pine.

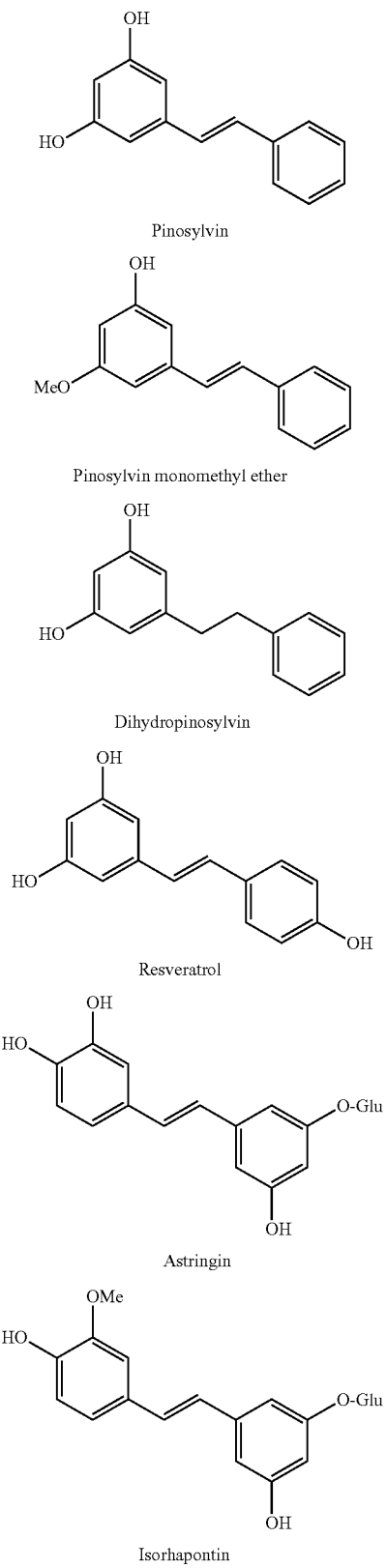

FIG. 2

Pinosylvin

Pinosylvin monomethyl ether

Dihydropinosylvin

Resveratrol

Astringin

Isorhapontin

-continued
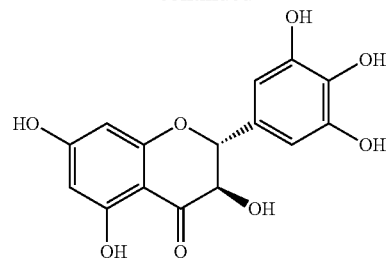
Dihydromyricetin
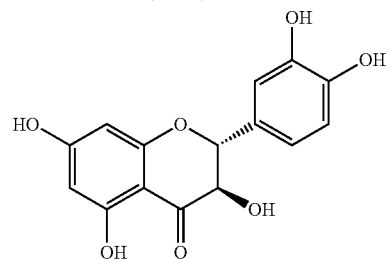
Taxifolin
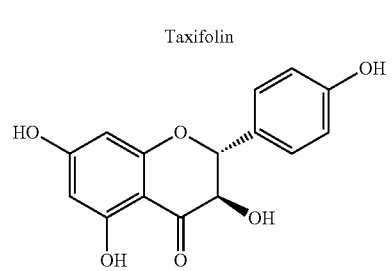
Dihydrokaempferol
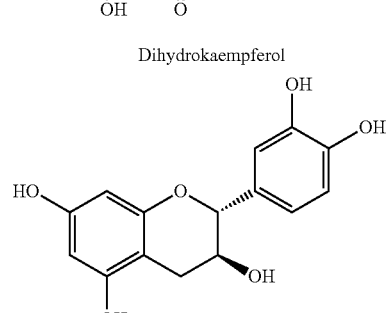
Catechin
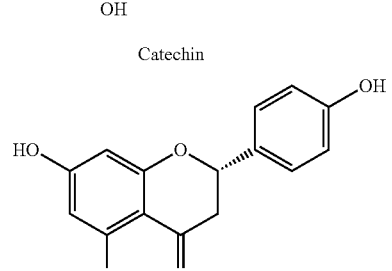
Naringenin
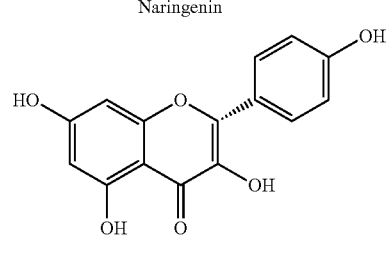
Kaempferol
-continued
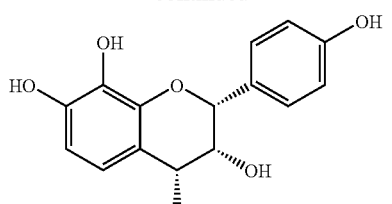
Teracacidin
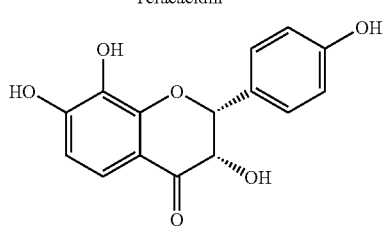
Keto-teracacidin
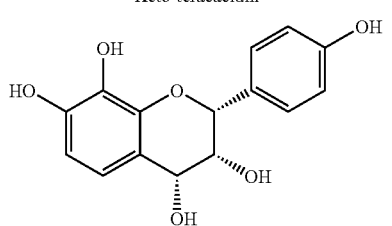
Isoteracacidin
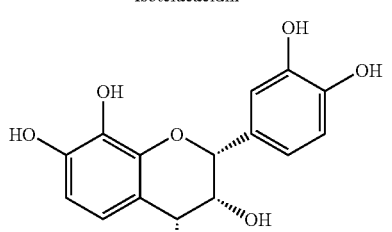
Melacacidin
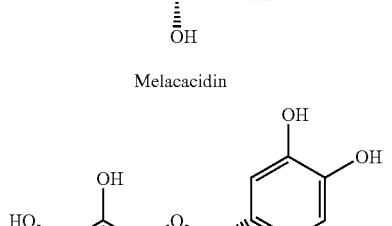
Isomelacacidin
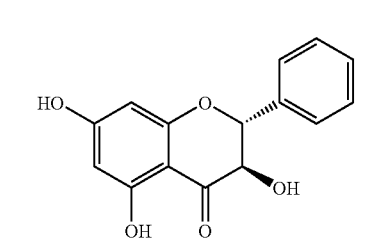
Pinobanksin

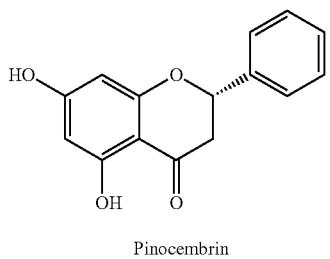

Pinocembrin

FIG. 2 illustrates different phenolic compounds that can be obtained by a hydrophilic extraction of wood material originated to stem knotwood or bark of pine.

As is apparent from FIG. 2 as well as from Table 1, pine stem knotwood and its bark contain several different stilbene compounds. Moreover, the percentual share of these stilbene compounds in the pine polyphenolic compounds present in stem knotwood and bark is remarkably high in comparison with the quantity of other polyphenolic compounds. Further, pine contains a remarkable quantity of various flavonoids.

In Tables 4A, 4B, 4C and 4D, there are represented antioxidative and free radical capturing effects of pure polyphenolic compounds and of unpurified polyphenolic compounds containing raw extracts obtained from wood bark and stem knotwood.

TABLE 4A

Antioxidative capacity of the lipids in polyphenols-bearing unpurified extracts obtained in hydrophilic extraction from stem knotwood or wood bark, as expressed in terms of extract concentration EC50 µg/L, which inhibits 50% of the peroxidation of lipids.

| | EC50 µg/L |
|---|---|
| stem knotwood obtained extracts | |
| Acacia crassicarpa | 19 |
| Abies pectinata | 21 |
| Picea glauca | 24 |
| Acasia mangium | 24 |
| Tsuga canadensis | 27 |
| Picea sitchensis | 28 |
| Tsuga heterophylla | 28 |
| Eucalyptus globulus | 57 |
| Abies lasiocarpa | 59 |
| Populus gradidentata | 61 |
| Pinus resinosa | 61 |
| Fagus sylvatica | 91 |
| Populus tremuloidis | 135 |
| Pinus strobes | 159 |
| Populus tremula | 317 |
| extracts obtained from wood bark | |
| Picea abies | 49 |
| Betula pendula | 81 |
| Pycnogenol | 84 |
| Pseudotsugamenziensii | 84 |
| Thuja occidentalis | 131 |
| Pinus banksiana | 143 |
| Populus tremula | 213 |
| Abies lasiocarpa | 316 |

TABLE 4B

Comparison of the antioxidative capacity of the lipids in pure polyphenol extracts isolated from certain wood materials, as expressed by the extract concentration EC50 µg/L, which inhibits 50% of the peroxidation of the lipids.

| Compound | EC50 µg/L |
|---|---|
| Cyclolariciresinol | 17 |
| Pinoresinol | 20 |
| Melacasidine | 36 |
| Secoisolariciresinol[1] | 37 |
| Taxifolin[1] | 46 |
| Pinosylvin | 50 |
| Teracasidine | 50 |
| Nortrachelogenin[1] | 53 |
| Hydroxymatairesinol[1] | 58 |
| Matairesinol[1] | 99 |
| Lariciresinol[1] | 126 |
| Dihydrokaempferol | 488 |
| Pinosembrin | 1135 |

[1]Willför et al,. J. Agric. Food. Chem, 51. 26 (2003).

Tables 4C and 4D further represent the free radicals capturing capacity of certain pure polyphenols and unpurified polyphenol extracts with respect to peroxide radicals.

TABLE 4C

Peroxide radicals/(mmol) capturing capacity of unpurified polyphenols-bearing extracts obtained in hydrophilic extraction from stem knotwood or wood bark, as expressed in capacity per gram of extract.

| | capturing capacity mmol/g |
|---|---|
| Wood material, extracts obtained from stem knotwood | |
| Acacia crassicarpa | 21 |
| Eucalyptus globulus | 7.8 |
| Picea glauca | 7.8 |
| Abies pectinata | 6.8 |
| Tsuga canadensis | 6.8 |
| Acasia mangium | 6.8 |
| Tsuga heterophylla | 5.8 |
| Larix lariciana | 5.8 |
| Larix sibirica | 5.8 |
| Picea mariana | 5.8 |
| Picea sitchensis | 4.9 |
| Pinus sylvestris | 4.9 |
| Thuja plicata | 3.9 |
| Populus gradidentata | 3.9 |
| Fagus sylvatica | 2.9 |
| Abies lasiocarpa | 2.7 |
| Pinus resinosa | 2.7 |
| Pinus banksiana | 1.9 |
| Pinus strobus | 1.1 |
| Populus tremuloidis | 0.39 |
| Populus tremula | 0.29 |
| Wood material, wood bark obtained extracts | |
| Pseudotsuga menziensii | 4.9 |
| Pycnogenol | 4.9 |
| Pinus banksiana | 3.1 |
| Betula pendula | 2.9 |
| Picea abies | 2.9 |
| Thuja occidentalis | 1.9 |
| Abies lasiocarpa | 0.58 |
| Populus tremula | 0.29 |

TABLE 4D

Comparison of the peroxide radicals (mmol) capturing capacity of certain pure polyphenol extracts isolated from wood material, as expressed per gram of extract.

| Compound | capturing capacity mmol/g |
| --- | --- |
| Melacasidine | 20 |
| Taxifolin[1] | 16 |
| Cyclolariciresinol | 12 |
| Secoisolariciresinol[1] | 8.5 |
| Pinoresinol | 7.8 |
| Tetra casidin | 7.8 |
| Nortrachelogenin[1] | 5.9 |
| Hydroxymatairesinol[1] | 5.6 |
| Matairesinol[1] | 2.9 |
| Lariciresinol[1] | 2.7 |
| Dihydrokaempferol | 0.78 |
| Pinosylvin | 0.78 |
| Pinosembrin | 0.49 |

[1]Willför et al,. J. Agric. Food. Chem., 51, 7600-7606 (2003).

Tables 4A and 4B represent the antioxidative effect of a few pure polyphenols and of unpurified polyphenolic compounds containing raw extracts, obtained from wood bark and stem knotwood. Tables 4C and 4D in turn illustrate the peroxide radicals capturing capacity of a few pure polyphenols and of unpurified, polyphenolic compounds containing raw extracts, obtained from wood bark and stemwood knot. In Tables 4A-4D, it can be observed that the antioxidative and free radical capturing properties of solutions containing pure polyphenol compounds, obtained from wood material in hydrophilic extraction, are often remarkably different from the corresponding properties of compound mixtures containing unpurified raw extract solutions and obtained from wood material in hydrophilic extraction, owing to the synergetic effects of the compounds contained in the compound mixtures in unpurified extracts. The compound mixtures according to the invention are obtained from these unpurified raw extract solutions.

The production method of a compound mixture according to the invention, and the polyphenolic compounds contained therein, as well as the mutual ratios of their quantities depend on the designed usage and on the availability of raw materials. The compound mixture according to the invention is often obtained from the material of two or more wood species. Thus for example wood processing industry generally uses both spruce and pine in the pulping process. The production of a mixture according to the invention can utilize knotwood or stem knotwood parts that are less suitable in the pulping process. However, because the pulping process mainly uses spruce and to a lesser amount pine, it is often more advantageous to form a compound mixture of spruce, which is more disadvantageous for the use of the composition, because it has better availability than pine. For example, a compound mixture obtained from pine wood knot material in hydrophilic extraction has a remarkably abundant quantity of stilbenes, which are effective microbicides and effective compounds inhibiting microbial growth. As for a compound mixture obtained from spruce wood knot material in a hydrophilic extraction, it contains a remarkable quantity of 7-hydroxymatairesinol, as well as its derivatives, such as matairesinol. Although the efficiency of 7-hydroxymatairesinol in many targets of usage is lower than that of stilbenes, particularly that of pinosylvin and its derivatives, it is profitable to use in the microbicidic compound mixture knot extract obtained from spruce, containing polyphenolic compound mixture where the major components are lignans, because said extract has better availability and thus generally lower price.

Production of the Compositions and their Semifinished Products

A phenolic compounds containing mixture according to the invention can be included in cosmetic and food technology compositions and their semifinished products in a way known as such, of which examples are also given below. Thus, in case a compound mixture is extracted for instance of wood material by an alcoholic solution into a raw extract, this raw extract can be made into a homogeneous mixture such as a homogeneous solution, or a colloidal dispersion with two or several phases such as gel, paste, emulsion, microemulsion, nanoemulsion suspension, dispersion or mist. In that case a phenolic compounds containing raw extract is included in a homogeneous solution by dissolving, and/or it is included by dispersing to the carrier agents of a colloidal mixture in a way known as such, so that the raw extract is admixtured either in a phase containing a continuous carrier agent, or to a phase containing a carrier agent to be dispersed. For forming a carrier of carrier agents, there are is used conventional auxiliary agents of the trade. Such agents are, among others, surface active agents, dispersing agents such as emulsifying agents, gel formers such as carbomers and methylcellulose.

The employed carrier agents are gel base formers such as water or alcohol, cream base and paste base formers such as paraffins, waxes, silicones, aqueous phase forming agents (water) or phase formers such as paraffin or stearic acid. The compositions can also be multi-phase compositions, so that the carrier agent is formed of several aqueous and/or oil phases. With respect to the manufacturing of various compositions, we refer to the literature of this field and to the examples to be given below.

In these homogeneous solutions and colloids, there can be admixtured additives such as UV protection agents, antioxidants and vitamins, surface active agents, moisturizing agents, moisture maintaining agents, stabilizing agents, moisture absorbing agents, emollients, fats, lubricants, perfumes, viscosity regulators, colorants, antioxidants and narrow-scale antimicrobial agents etc., in a conventional way known as such, with respect to which we refer to the literature of this field.

In case the composition is a packing material composition, the carrier agent is a packing material, in which the compound mixture contained in the extraction solution is impregnated or spread on. Said packing material can be cardboard, corrugated board, plastic admixtured cardboard or other packing material known from the prior art.

The effective agents, such as a UV protection agent, antioxidants and vitamins are added in the composition in the same way as the above mentioned additives.

In case the composition is a technical composition, the carrier is a commercial solvent, cleaning device such as a cleaning cloth, solid substance such as a powder used as a surface treatment agent, or a solution meant for the cleaning of a mammal's body. In the carrier, there is impregnated or otherwise included the compound mixture according to the invention.

Surface active agents applicable in exemplary liquid compositions according to the invention, and in their semifinished compositions are: tensides, lecithin, caprylic acid and monoglycerides and diglycerides of capric acids, polyglyceryl-3-di-isostearate/polyglyceryl-2 and polyhydroxystearate, alkyl glycoside/alkyl alcohol, cetearyl pyridium chloride, bentsalkonium chloride, ionogenic agents, cetearyl glycosides, lower alcoxilated glycosides and micelle-forming agents.

Perfumes can be selected for example from a group including phenyl ethyl glycol, eugenol, isoeugenol, geraniol, citronellol or linalool, or their esterized forms or their aldehydes.

Colorants can be selected for example from among the colorants accepted by FDA to be used in foodstuffs and cosmetic products.

In compositions according to the invention, as well as in their semifinished products, it is also possible to add other effective agents as additives. Such effective agents to be used as additives are for example antioxidants. Among antioxidants, let us point out natural and synthetic vitamins such as vitamin A, B, C. D, E, provitamin B5, vitamin B3, L-ascorbic acid and vitamin E; further, there can be used antioxidants obtained from natural sources, such as antioxidants contained in green tea, antioxidants contained in flaxseed, antioxidants contained in horse chestnut, beta carotene, selenium, glutamine, ubiquinone (coenzyme Q10), glycolic acid, growth hormones and kinetin.

An advantageous botanical microbial growth inhibiting agent is betulinic acid, betuloinic acid or betulonic acid (U.S. Pat. No. 6,280,778), derivatives of betuligenolin, and resvatrol obtained from spruce bark. These have been found to have an antimicrobial effect, and their cytotoxicity for healthy cells is low, and they enhance the dying of cancer cells. These can be added, either as pure compounds or as unpurified extract solutions obtained from wood bark, or as powders, in compositions and semifinished products to be manufactured according to the invention.

Further, in compositions to be manufactured according to the invention, there can also be added pure flavonoids, lignans and stilbenes as well as their oligomers isolated from plants. In this application, the term 'oligomers' refers to homologs of a compound, i.e. to its dimers, trimers etc., where the included number of similar units is lower than in a polymer. Suitable botanical polyphenol compound sources are oilseeds, nuts, grain, fruits, berries and pulses.

EXAMPLES

Field Tests

A) Cytotoxicity in Comparison with BHT

Table 1 shows comparisons between the cytotoxicity of a compound mixture according to the invention and the cytotoxicity of an antioxidant (BHT) that is widely used in food and cosmetic industry.

TABLE 5

The cytotoxicity of sample extracts, alcohol-extracted from spruce stem knotwood chips, containing the compound mixture, or a powder obtained by pulverizing spruce stem knotwood chips and containing the compound mixture, in comparison with the cytotoxicity of BHT (butylated hydroxytoluene). The composition of the individual compounds included in the compound mixture contained by the samples was in accordance with Table 2A. The cytotoxicity of the sample extracts and powders for human keratinocyte cells was measured. The employed measure of cytotoxicity was the total protein quantity created by the samples, when the samples were incubated together with human keratinocyte cells for a certain incubation time (24 h). For each sample, there was searched a limit value (EC20), by which 20% of the cultivated cells died.

| Extraction solvent | sample | EC20 ppm 24 h |
|---|---|---|
| pentylene glycol | HMR-5 | 450 |
| butylene glycol | HMR-4 | 600 |
| glycerol | HMR | 1.260 |
|  | HMR powder | 160 |

TABLE 5-continued

The cytotoxicity of sample extracts, alcohol-extracted from spruce stem knotwood chips, containing the compound mixture, or a powder obtained by pulverizing spruce stem knotwood chips and containing the compound mixture, in comparison with the cytotoxicity of BHT (butylated hydroxytoluene). The composition of the individual compounds included in the compound mixture contained by the samples was in accordance with Table 2A. The cytotoxicity of the sample extracts and powders for human keratinocyte cells was measured. The employed measure of cytotoxicity was the total protein quantity created by the samples, when the samples were incubated together with human keratinocyte cells for a certain incubation time (24 h). For each sample, there was searched a limit value (EC20), by which 20% of the cultivated cells died.

| Extraction solvent | sample | EC20 ppm 24 h |
|---|---|---|
| propylene glycol | HMR-3 | 620 |
| ethanol | HMR extract | 550 |
| ethanol | BTH | 5.50 |

From Table 5 it can be observed that the most cytotoxic substance was BTH, which was 10-20 times more cytotoxic than HMR powder. HMR powder was obtained by pulverizing spruce stem knotwood without other further cleaning, and said powder contained mainly 7-hydroxymatairesinol as well as, to a lesser degree, other polyphenolic lignans. Other knot extracts obtained from spruce knotwood chips by hydrophilic extraction with alcohol (ethanol, propylene glycol, pentylene glycol, butylene glycol, or glycerol) also contained lignan mixtures according to the invention, which included, as their principal component, 7-hydroxymatairesinol and also other phenolic lignans. With respect to HMR extract mixtures, BTH was 50-100 times more cytotoxic.

B) The Growth-Inhibiting Effect Against the Micro-Organisms

Test 1

The antimicrobial effect of a few compound mixtures according to the invention against bacteria, yeast and fungi was examined:
  raw extracts extracted from spruce stem knotwood chips by 4-glycol (sample 1), 5-glycol (sample 2) and 3) glycerine (sample 3) and glycerol (sample 4), containing 10 wt % of the compound mixture, the composition of the polyphenolic compound mixture of said raw extracts being in accordance with Table 2A (contained mostly 7-hydroxymatairesinol).
  combined raw extract (sample 5), extracted from spruce stem knotwood chips and pine stem knotwood by ethanol (pine) and by butylene glycol (spruce), containing roughly 10 wt % of the compound mixture obtained from pine and spruce. The sample compound mixtures contained both a lignan mixture obtained from Norway spruce (*Picea abies*), the composition of which was in accordance with Table 2A, and a mixture of lignans and stilbenes obtained from pine (*Pinus sylvestris*), the composition of which roughly corresponded to the one illustrated in Table 1 (test 2, ethanol extraction).

The growth-inhibiting effect of the compound mixture samples was verified against the following micro-organisms:
*Staphylococcus aureus* ATCC 6538
*Esterichia coli* ATCC 8739
*Pseudamonas auriginosa* ATCC 9027
*Pseudamonas putida* ATCC 49128
*Klebsiella pneumoniae* ATCC 10031
*Candida albicans* ATCC 10231
*Malassezia furfur* ATCC 96809 (yeast fungus)
*Aspergillus niger* ATCC 16404

Performance of the Study

In each of the 10 g sample batches taken from the samples, there were added different microbe cell suspensions, where the microbe population density was at least $5\times10^6$ microbes/ml. The sample batches were incubated at room temperature (22° C.) for 2, 4, 24 and 48 hours, 4 days, 7 days, 14 days and 28 days.

When reproductive microbes were not found in the samples anymore, each sample was cultivated for a 1 ml sample batch in a 100 ml Letheen broth base, and after concentration, possible bacterial growth was further checked on a culture base.

Results

All samples had an extremely good growth-inhibiting effect against micro-organisms; after an incubation time of 4 hours, 24 hours, 48 hours, 7 days, 14 days and 28 days, microbial growth was not detected.

Both the raw extracts obtained from spruce material according to the invention by alcohol extraction, and the raw extracts obtained from pine material by alcohol extraction, as well as the raw extracts obtained from a combined spruce and pine material by alcohol extraction prevented the growth of antimicrobial agents on a wide scale. They prevented the growth of both Gram-negative bacteria *E. coli, Ps. aeruginosa, Ps. putida, Kl. pneimoniae*) and Gram-positive bacteria (*S. aureus*). In addition, they also efficiently prevent the growth of yeasts (*M. furfur, C. albicans*) and fungi (*A. niger*).

Test 2

Raw extract extracted from spruce stem knotwood with pentylene glycol, containing a 10 wt % compound mixture of phenolic compounds, the composition of which was in accordance with Table 2A, was added in a sun protection cream for 3 wt %. Ethylhexyl glycerine (EH), efficient against Gram-positive bacteria, was mixed into the same sun protection cream for 0.3 wt % and 0.5 wt %. For the sake of comparison, to the same sun protection creams there was added a conventionally used, widely antimicrobial agent, phenoxyethanol (FE), which has a relatively low highest acceptable quantity of usage owing to its cytotoxicity and skin irritative properties.

| Test | number of inoculation cycles | | | | | | |
|---|---|---|---|---|---|---|---|
| | 0 | 1 | 2 | 3 | 4 | 5 | 6 |
| Test 1 cream base 0.3 wt % EH 1 wt % FE | – | – | – | +Y | +M, Y | +M, Y | ++M, Y |
| Test 2 Cream base 0.5 wt % FE 1 wt % EF | – | – | – | – | – | – | – |
| Test 3 Cream base 0.3 wt % EH 3 wt % HMR-5 | – | – | – | – | – | – | – |
| Test 4 Cream base 0.35-% EH 3 wt % HMR-5 | – | – | – | – | – | – | – |

Y = yeast growth
M = Fungal growth
– no microbial growth
+ slight microbial growth
++ moderate microbial growth As is apparent from the above described test 2, when a 3 wt % raw extract, containing about 10 wt % of compound mixture, obtained from spruce stem knotwood was used in a sun protection cream instead of phenoxyethanol, it was possible to maintain a wide-scale effect against microbial growth. The effect was maintained, although the content ethylhexyl glycerine, inhibiting the growth of Gram-positive bacteria, was reduced, which shows that the raw extract from spruce stem knotwood itself has a Gram-positive bacteria growth-inhibiting effect.

The sun protection cream used in the above described test was a cream according to example 2. When using phenoxyethanol, the highest acceptable content of which is 1 wt %, there was detected a growth of yeasts and fungi with an ethylhexyl glycerine content of 0.3% in the sun protection cream. On the other hand, with an ethylhexyl glycerine content of 0.5%, the growth of yeasts and fungi was inhibited. When phenoxyethanol was replaced by a lignan mixture HMR-5 obtained from spruce stem knotwood with hydrophilic extraction (pentylene glycol), it was observed that the ethylhexyl glycerine content could be reduced to 0.3%, and yet the microbial growth in the cream was inhibited. Thus the alcohol extract (HMR-5) according to the invention, which contains a physiologically well-tolerated mixture, can be used to replace the antimicrobial phenoxyethanol, the use of which is restricted owing to its physiological toxicity. The composition HMR-5 was in accordance with the composition according to Table 2A.

Increasing the in vivo-Protective Factor of Sun Protection Composition

For a sun protection cream according to example 4, in which there was mixed raw extract for 3 wt %, said raw extract being obtained by extracting chips from stem knotwood of spruce by pentylene glycol, there was tested the protective factor (SPF) both in vitro and in vivo.

The protective factor in vivo was defined on the skin of 5 test persons according to the method "International SPF test method 2006" (International SPF test method 2006, CTFA South Africa, JCIA and CTFA, 2006). The radiation source used for UV irradiation was "Multiport Solar UV Simulator Type 601-150". The in vivo protective factor obtained for the sun protection composition by this method was 61.0.

For a similar sun protection composition, the obtained in vitro protective factor, by the "Diffrey-Robson" standard method, was 40.

Production of the Compositions and their Semi-Finished Products

Example 1

Semi-finished product: semifinished product with a UV protection profile similar to that of melanin.

Pigment-quality $TiO_2$ and extremely finely divided $TiO_2$, as well as pigment-quality iron oxide is coated for example with aluminum oxide and with a mixture of polyphenolic compounds according to the invention, which mixture has antioxidative and/or free radical capturing properties. The mineral UV protection agents ($TiO_2$ and iron oxide) to be coated are dispersed to an oil phase, such as isononyl-isononanoate, by means of a surface active compound. A suitable compound mixture of polyphenolic compounds is for example a lignan mixture extracted from spruce knotwood material by butylene glycol or pentylene glycol, which contains 7-hydroxymatairesinol as its principal component, and where the polyphenolic compounds contained by the compound mixture are similar to those represented in Table 2A, so that the relative quantities of the polyphenolic compounds contained in the compound mixture are mutually similar to those represented in Table 2A

Example 2

Semifinished product: inorganic semifinished product containing UV protection agent.

The semifinished product contains inorganic and/or organic UV protection agents, such as $TiO_2$ or $TiO_2$ and ZnO, as well as possibly organic MBBT absorbing radiation within the UVA and UVB ranges. Inorganic UV protection agents are coated with aluminum oxide or silica, and in the coating, there is included a mixture according to the invention, containing polyphenolic compounds. Here a suitable compound mixture is for example a solution extracted from knotwood material of *picea abies*, first by hexane and then by butylene glycol, which contains 7-hydroxymatairesinol and other lignans. As the principal component, the raw extract contained 7-hydroxymatairesinol and also lesser but still detectable quantities of lariciresinol, conidendrin and oligolignans. Inorganic UV protection agents are coated in an oil dispersion, where the continuous phase is for example a dimeticon or isononyl-isononanoate, in the presence of a suitable surface active agent.

In the semifinished products of both Example 1 and Example 2, the inorganic UV protection agent is well protected by a compound mixture of polyphenolic compounds according to the invention, and it can neither induce the creation of free radicals nor be itself transformed into a free radical. The polyphenolic compound mixture present in the coating of the UV protection agent is itself stabile, and it also has UV radiation absorbing properties, which means that it can be used for modifying the UV radiation absorption profile of the compositions within the UVA and UVB ranges.

Example 3

UVA/UVB Sun Protection Lotion, O/W Type, with TINOSORB® M

Lotion with a very high SPF and excellent UVA protection due to the photostable UVA filter TINOSORB® M. This emulsion is smooth and spreads easily. SPF in vivo=38, broadband.

This lotion includes UVA filter TINOSORB® M and also 10 wt-% Wood Knot Extract in Glycerine, which will enhance in vivo SPF by trapping possible free radicals including reactive oxygen and lipid radicals induced by solar ultraviolet radiation or particles from organic UV filters.

Composition

|  | Trade name | Inci Name | Supplier | % w/w (as supplied) |
|---|---|---|---|---|
| Part A | Amphiosol K | Potassium Cetyl Phosphate | Roche | 2.00 |
|  | Antaron WP-660 | Tricontanyl PVP | ISP | 1.00 |
|  | Myritol 318 | Caprylic/Capric Triglyceride | Cognis | 5.00 |
|  | Crodamol AB | C12-15 Alkyl Benzoate | Croda | 5.00 |
|  | Cetiol SN | Cetearyl Isononanoate | Cognis | 5.00 |
|  | Cutina GMS | Glyceryl Stearate | Cognis | 3.00 |
|  | Lanette 16 | Cetyl Alcohol | Cognis | 1.00 |
|  | Dow Corning 200 Fluid 350 cs | Dimethicone | Dow Corning | 0.10 |
|  | TINOSORB ™ OMC | Ethylhexyl Methoxycinnamate | Ciba Specialty Chemicals | 5.00 |
| Part B | Water | Water |  | q.s. to 100 |
|  |  | 10% Extracted Spruce and/or Pine knot mixture in Glycerine | Granula Ltd | 3.00 |
| Part C | SALCARE® SC80 | Steareth-10 Allyl Ether/Acrylates Copolymer | Ciba Specialty Chemicals | 0.50 |
| Part D | TINOSORB® M | Methylene Bis-Benzotriazolyl Tetramethylbutylphenol (and) Aqua (and) Decyl Glucoside (and) Propylene Glycol (and) Xanthan Gum | Ciba Specialty Chemicals | 20.00 |
| Part E | Phenonip | Phenoxyethanol (and) Methylparaben (and) Ethylparaben (and) Butylparaben (and) Propylparaben (and) Isobutylparaben | Clariant | 0.30 |
| Part F | Sodium Hydroxide (Solution 10%) | Water (and) Sodium Hydroxide |  | q.s. to pH 7.00 |
| Part G | Fragrance | Fragrance |  | q.s. |

Technical Data

| pH value | 7.00 |
|---|---|
| Appearance | white lotion |
| Viscosity (Brookfield DVIII + LV4/80 rpm) | 3000 mPas |
| UVA/UVB ratio*/Critical Wavelength* | 0.75/384 nm |

Technical Data

| pH value | 7.00 |
|---|---|
| Appearance | white lotion |

-continued

| | |
|---|---|
| Viscosity (Brookfield DVIII + LV4/80 rpm) | 3000 mPas |
| UVA/UVB ratio*/Critical Wavelength* | 0.75/384 nm |

Example 4

Sun Protection Cream

In this sun protection cream, in order to obtain a wide-scale antimicrobial effect, there was used a compound mixture (HMR-5) extracted from stem knotwood chips from *picea abies* in pentylene glycol. HMR-5 was an unpurified raw wood knot extract and contained 10 wt % of the compound mixture and 90 wt % of pentylene glycol. At the same time, HMR-5 also served as a trapper of free radicals induced by possible sunlight or by particles released from an organic UV protection agent, thus increasing the in vivo protective factor on the skin. The extract also stabilizes vitamine C. The sun protection cream contained UV protection agents that protect the skin both against UVA and UVB rays (Granlux GA12-45 and an organic protection agent).

| Part 1 | |
|---|---|
| Granlux ® GA12-45: (Granula Ltd) Concentrate containing inorganic UVprotection agents (TiO$_2$ and ZnO) protected by aluminum oxide, dispersed in dimethicone and surface active dispersing agent | 28% |
| Glycerine | 4% |
| Part 2 | |
| alpha-Bisapolol | 1.5% |
| *Bytospermum parkii* Fruit | 1.5% |
| Cetiol CC | 0.1% |
| Oxynex K Fluido (vitamine blend) | 0.1% |
| Alkyl benzoate | 4% |
| Part 3 | |
| Water | 23.5% |
| *Aloe barnadensis* | 1% |
| Multivitamin product | 0.3% |
| Dinatrium EDTA | 0.1% |
| Part 4 | |
| Cyclomethicone | 1.5% |
| Ethylhexyl methoxycinnamate | 5% |
| Organic UV protection agent | 2% |
| Homosalate | 5% |
| Part 5 | |
| Ethylhexyl glycerine | 0.5% |
| HMR-5 (intermediate product of example 1) | 3% |

Parts 1-5 were mixed as a sun protection cream by conventional methods.

Example 5

Cleaning Cloth Containing Antimicrobial Compound Mixture According to the Invention This can be manufactured as is described in the U.S. Pat. No. 6,287,582. The cloth contains a water-insoluble carrier and a cosmetic composition impregnated in the carrier, including a compound mixture according to the invention, pH regulator such as alpha- or beta-hydroxycarboxylic acid, silicone microemulsion and surface active agent. The pH of the cosmetic composition in water is no more than 6. The microemulsion is for example a dimethiconol microemulsion.

In the Table below, there are given two exemplary compositions to be impregnated in a cleaning cloth, containing an extract mixture according to the invention.

| Ingredient | Acceptable range (Percent by weight) |
|---|---|
| Dual chain quaternary (N-alkyl dimethyl Ethylbenzyl chloride or N-alkyldiemethyl Ethylbenzyl ammonium chloride) | 0.0-2.0 |
| Ortho phenyl phenol | 0.0025-2.0 |
| Paratertiary amyl phenol | 0.0025-2.0 |
| Extracted knot mixture in alcohol (spruce, Granula Ltd) | 1.0-40.0 |
| Tergitol 15-S-5 | 0.5-2.0 |
| Citric acid | 0.1-2.0 |
| Emollient | 0.1-3.0 |
| Water | Up to 100 |

| Ingredient | Specific composition formulation (Percent by weight) |
|---|---|
| Dual chain quaternary (N-alkyldimethylethylbenzyl chloride or N-alkyldimethylethylbenzyl ammonium chloride) | 0-0.25 |
| Ortho phenyl phenol | 0.0125 |
| Paratertiary amyl phenol | 0.0025 |
| Extracted knot mixture in alcohol (Granula Ltd) | 0.01-40.0 |
| Tergitol 15-S-5 | 0.5 |
| Citric acid | 0.05 |
| *Aloe vera* gel | 1.0 |
| Water | Up to 100 |

Example 6

This formulation is good for wound healing and skin remedy

Aftershave Gel without Alcohol

| Trade name/INCI | wt % |
|---|---|
| A | |
| Carbopol 940/Carbomer | 0.30 |
| Water dem. Aqua dem. | 40.00 |
| B | |
| Cremophor CO 40/PEG-40/Hydrogenated castor oil | 3.00 |
| Perfume | q.s. |
| Menthol | 0.10 |
| D-Panthenol 50 P/Panthenol, | 0.10 |
| 10% Extracted Spruce and/or Pine knot mixture in propylene glycol | 4.00* |
| Triethanolamine | 0.40 |
| Water Aqua dem. | up to 100% |

Production
Let phase A swell. Phase B is dissolved and mixed in phase A.
Viscosity: roughly 4 000 mPa s (Brookfield RVT), pH value roughly 7.
*a mixture of phenolic compounds obtained from stem knotwood chips in propylene glycol extraction, contg. 10 wt % of the compound mixture and 90 wt % of propylene glycol.

Example 7

Rehydrating Aftersun Mist

In the production of this aqueous mist-like composition, there was used a water component, emulgator (Luviquat®Mono CP) and PEG-40, a surface active silicone-based agent (Dow Corning 190 Surfactant), a moisturizer (D-panthenol), and a moisturizing agent Prodew® 200. The growth of micro-organisms was inhibited by a mixture of phenolic compounds, obtained in pentylene glycol extraction from chips contained in spruce stem knotwood in mixture, contg. 10 wt % of the compound mixture and 90 wt % of propylene glycol. This raw extract was used unpurified in the production of mist.

| Trade name/INCI | wt % |
|---|---|
| A | |
| Deionized water | 89.10 |
| Luviquat ® Mono CP/Hydroxyethyl cetyl dimonium phosphate (1) | 2.00 |
| D-Panthenol (1) | 0.50 |
| 10% Extracted knot mixture in pentylene glycol (5)*' | 5.50 |
| Dow Corning 190 Surfactant/Dimethicone polyol (2) | 0.50 |
| Prodew ® 200/Sodium lactate & Sodium PCA & Sorbitol & Hydrolyzed Collagen & Proline (3) | 2.00 |
| B | |
| Cremophor ® RH 40/PEG-40, Hydrated castor oil (1) | 0.30 |
| Perfume | 0.10 |

*polyphenolic compound mixture obtained from wood chips (spruce) contained in stem knotwood in pentylene glycol extraction, contg. 10 wt % of the extracted compound mixture and 90 wt % of propylene glycol.
Production
Combine ingredients of phase A and stir until solution is clear.
Combine ingredients of phase B. Melt hydrated castor oil and stir with perfume.
Combine phase B with A and stir until mixture is clear.
pH of the end product is 6.
Suppliers
(1) BASF
(2) Dow Corning
(3) Ajinomoto
(4) Nipa
(5) Granula Ltd

Example 8

Body Milk

The body milk according to Example 6 is an aqueous emulsion, in the manufacturing of which there are used emulsifying agents (Cremophor), auxiliary agent (glyceryl monostearate) as well as water and oil components, viscosity regulator (cetyl stearyl alcohol), emollients (Luvitol EHO) and conditioner (Luviquat PQ 11). The growth of micro-organisms was inhibited by a mixture of phenolic compounds obtained from spruce stem knotwood in butylene glycol extraction, which compound mixture contained phenolic compounds 10 wt %, and which raw extract was used unpurified for the production of body milk.

| Trade name/INCI | wt % |
|---|---|
| A | |
| Cremophor A 6/Ceteareth-6, Stearyl alcohol | 1.00 |
| Cremophor A 25/Ceteareth-25 | 1.00 |
| Glyceryl monostearate | 2.00 |
| Cetyl stearyl alcohol | 2.00 |
| Paraffin oil/Mineral oil | 3.00 |
| Luvitol EHO/Cetyl stearyl octanoate | 5.00 |

-continued

| Trade name/INCI | wt % |
|---|---|
| B | |
| 10 wt % Extracted knot mixture in butylene glycol* | 5.00 |
| Luviquat PQ 11 (1) Polyquaternium-11 | 4.00 |
| Water | 77.00 |
| C | |
| Perfume | q.s. |

**polyphenolic mixture obtained from wood chips (spruce) contained in stem knotwood in butylene glycol extraction, contg. 10 wt % extract mixture and 90 wt % butylene glycol.
Production
Mix phases A and B separately at roughly 80° C. Mix phase B to phase A whilst homogenizing, and continue homogenizing for a while. Cool roughly at 80° C., add phase C and homogenize again.
Viscosity: roughly 3000 mPas
pH: roughly 6

Example 9

Concentrated Powder

| Trade name/INCI | wt % |
|---|---|
| A | |
| Talcum | 72.00 |
| Magnesium stearate | 10.00 |
| Calcium carbonate | 2.00 |
| Sicovit White E 171/C,I. 77891/Titanium oxide | 9.00 |
| Sicovit Brown 70 E 172/Ferric oxides | 1.00 |
| Powdered knot mixture (spruce) | 5.00 |
| B | |
| Paraffin oil/Mineral oil | 0.50 |
| Vaseline/Petrolatum | 0.50 |

Production
Mix ingredients of phase A and homogenize. Stir phase B to phase A and mix again.

Example 10

Cell-Protective Composition

| Trade name, compound/INCI | wt % |
|---|---|
| A | |
| RonaCare ™ Ectoin (1) | 1.00 |
| 10% Extracted Spruce and/or Pine knot mixture in Pentylene Glycol (5) | 3.00 |
| Water, mineralized | up to 100% |
| B | |
| Sisterna SP30-C (2)/saccharose distearate | 2.70 |
| Sisterna SP70-C (2)/saccharose stearate | 0.90 |
| Cetiol OE (3)/dicapryl ether | 5.00 |
| Miglyol 812 (1)/kaprylic/kapric triglyceride | 2.00 |
| Isopropyl palmitate (3)/isopropyl palmitate | 2.00 |
| Cegesoft C 24 (3)/ethylhexyl palmitate | 7.00 |
| Carbopol ETD 2001 (4)/carbomer | 0.20 |

| Trade name, compound/INCI | wt % |
|---|---|
| C | |
| Sodium hydroxide, 10% solution (1)/sodium hydroxide q.s. | |

Production
Heat phase A to 75° C., disperse phase B and heat to 75° C., add phase B to phase A, homogenize, adjust pH with sodium hydroxide, cool to room temperature by stirring simultaneously.
Note
pH (22° C.): 6.50
Viscosity (21° C.): 109 000 mPa · s (Brookfield RVT, spindle C, 5 rpm, Helipath)
Suppliers
(1) Merck KGaA/Rona ®
(2) Sisterna C.V./Dai-Ichi
(3) Cognis GmbH
(4) B F Goodrich GmbH
(5) Granula Ltd

Example 11

Night Care Cream

For producing this cream-like composition, there was used a water component, emulsifying agents (PEG-7), emollients (Luvitol EHO), wax components and fungicidal and moisturizing agents (jojoba oil). The growth of antimicrobial agents was prevented by jojoba oil and by a mixture of phenolic compounds, obtained from spruce stem knotwood in glycerine extraction, which compound mixture contained phenolic compounds 10 wt %, and which raw extract was used unpurified for producing the cream.

| Trade name/INCI | wt % |
|---|---|
| A | |
| Cremophor WO 7/PEG-7 Hydrated castor oil | 6.00 |
| Luvitol EHO/Cetearyl octanoate | 5.00 |
| Permulgin 3220/Microcrystalline wax | 2.00 |
| Beeswax | 0.50 |
| Cetiol SB 45/Shea Butter (*Butyrospermum parkii*) | 0.50 |
| Jojoba oil/Jojoba (*Buxus chinensis*) oil | 2.00 |
| Paraffin oil/Mineral oil | 10.00 |
| B | |
| 10% Extracted knot mixture in glycerin | 5.00 |
| Water | 67.00 |
| C | |
| Sodium ascorbyl sorbate | 2.00 |
| Perfume | q.s. |

Production
Mix phases A and B separately to roughly 80° C. Stir phase B to phase A whilst homogenizing, continue homogenizing for a while. Cool to roughly 40° C., add C and homogenize again.

Example 12

Night Care Cream

The night care cream according to example 10 was almost identical to night care cream of example 9, but instead of sodium ascorbyl sorbate of example 9, sodium ascorbyl phosphate was used in example 12. The wood knot extract stabilizes the vitamine and provides preservation and improves antioxidant action.

| Trade name/INCI | wt % |
|---|---|
| A | |
| Cremophor WO 7/PEG-7 Hydrogenated Castor Oil | 6.00 |
| Luvitol EHO/Cetearyl Octanoate | 5.00 |
| Permulgin 3220/Microcrystalline Wax | 2.00 |
| Beeswax | 0.50 |
| Cetiol SB 45/Shea Butter (*Butyrospermum parkii*) | 0.50 |
| Jojoba Oil/Jojoba (*Buxus chinensis*) Oil | 2.00 |
| Paraffin Oil/Mineral Oil | 10.00 |
| B | |
| 10% Extracted Spruce and/or Pine knot mixture in glycerine | 5.00 |
| Water | 67.00 |
| C | |
| Sodium Ascorbyl Phosphate | 2.00 |
| Perfume | q.s. |

Production
Heat phases A and B separately to about 80° C. Stir phase B into phase A whilst homogenizing and continue homogenizing for a while. Cool to about 40° C., add phase C and homogenize again.

Example 13

Softcream with Vitamin E

For making softcream of example 13, there were used several emollients, oil and water components, preservatives, adjuvants and other additives including vitamins for antioxidant purpose. Antioxidative properties of vitamins was enhanced by adding a mixture of 10 wt % raw wood knot extract (from spruce and pine) including phenolic compounds in Glycerin (10 wt % of mixture of compounds and 90 wt % of glycerin). This glycerin containing raw-extract was used without further purification. The reactions of vitamins are generally slow and therefore they are not able to function in every environment sufficiently.

| Trade name/INCI | wt % |
|---|---|
| A | |
| Cremophor GO 32/Polyglyceryl-3 Dioleate | 0.75 |
| Luvitol EHO/Cetearyl Octanoate | 7.50 |
| Finsolv TN/Alkyl Benzoate | 5.00 |
| Miglyol 812/Caprylic/Capric Triglyceride | 4.00 |
| Abil EM 90/Cetyl Diethicone Copolyol | 2.25 |
| Abil 350/Dimethicone | 1.50 |
| Ascorbyl Palmitate, Citric Acid, Glyceryl Stearate, Propylene Glycol | 0.20 |
| B | |
| 10% Extracted Spruce and/or Pine knot mixture in Glycerin | 0.75 |
| Sodium Hydroxide | 0.25 |
| D-Panthenol USP/Panthenol | 1.50 |
| Sodium Chloride | 1.50 |
| EDTA | 0.1 |
| Preservative | q.s. |
| Water | 69.80 |

-continued

| Trade name/INCI | wt % |
|---|---|
| C | |
| (−)-Alpha-Bisabolol nat./Bisabolol | 0.10 |
| Vitamin A Palmitate 1 Mio./Retinyl Palmitate | 0.10 |
| Vitamin E Acetate/Tocopheryl Acetate | 5.00 |
| Perfume | q.s. |

Production
Heat phases A and B separately to about 80° C. Stir phase B into phase A whilst homogenizing. Cool to about 40° C., add phase C and homogenize again.
Viscosity: approx. 18 000 mPas

Example 14

Multi-Vitamin Cream, TYP W/O Formula

For manufacturing this W/O-type cream composition water and oil were used as carrier agents, as an adjuvant emulgators (PEG-7, PEG-45, Claytone XL) and as an additive moisturizer (Jojoba oil,) perfume and vitamins (sodium ascorbyl phosphate and retinol). Antioxidative and radical trapping capacity of vitamins was modified by a mixture of 10 wt % extracted knot mixture (spruce) containing phenolic compounds extracted from spruce knots into butylene glycol (ca 10 wt % of mixture of phenolic compounds and 90 wt % of butylene glycol). This raw-extract was used without further purification. Vitamins and extracted compound mixture in wood knot extract have a different time scale during which they will trap free radicals and therefore they complete each other. The wood knot extract will also protect vitamines like vitamine C from destabilisation.

| Trade name/INCI | wt % |
|---|---|
| A | |
| Cremophor WO 7/PEG-7 Hydrogenated Castor Oil | 6.00 |
| Paraffin Oil/Mineral Oil | 10.00 |
| Vaseline/Petrolatum | 3.00 |
| Miglyol 812/Caprylic/Capric Triglyceride | 5.00 |
| Elfacos ST 9/PEG-45/Dodecyl Glycol Copolymer | 2.00 |
| Jojoba Oil/Jojoba (*Buxus Chinensis*) Oil | 5.00 |
| Claytone XL/Quaternium-18 Bentonite | 1.00 |
| B | |
| 10% Extracted wood Knot mixture in Butylene Glycol | 4.00 |
| EDTA | 0.10 |
| Water | 61.90 |
| C | |
| Sodium Ascorbyl Phosphate | 1.00 |
| Retinol | 1.00 |
| Perfume | q.s. |

Production
Heat phases A and B separately to about 80° C. Stir phase B into phase A whilst homogenizing and continue homogenizing for a while. Cool to about 40° C., add phase C and homogenize again.
Viscosity: approx. 14 000 mPa s (Haake Viscotester VT-02).

Example 15

GAI-45 TS High SPF Cream

This composition was made of water phase, semifinished composition of GranLux® GAI-45 TS which is an W/O emulsion including UV protective agent (TiO$_2$ filter) in a silicon emulsifier system and 10 wt % extracted wood knot mixture of phenolic compounds originating to spruce knots and extracted into pentylene glycol (10 wt % of mixture of phenolic lignan compounds and 90 wt % of pentylene glycol). The extracted (wood) knot mixture will protect the coating of TiO$_2$ filter preventing particles of UV filter to induce free radicals at skin. The end composition included also emollient and dispersive oil (isononyl-isononanoate) and perfume.

| Trade name/INCI | Amount (%) | Manufacturer |
|---|---|---|
| A | | |
| GranLux ® GAI-45 TS | 25.0 | Granula Ltd |
| 10% Extracted knot mixture in pentylene Glycol | 3.0 | Granula Ltd |
| B | | |
| Water | 10.0 | |
| C | | |
| Isononyl Isononanoate | 22.0 | Seppic |
| D | | |
| Water | 39.0 | |
| Perfume | q.s. | |

1) Mix A at room temperature.
2) Prepare B and add it to A. Mix ca 3-5 min until all water has been taken up. The water will go in by diffusion, hydrate the polar parts and form the liquid crystalline phase. The polar phase and the hydrophobic phase seem initially to be totally separated but the water phase will be taken up by time and mixing.
3) Add to C to A + B while mixing. Viscosity goes down.
4) Add D to C + A + B slowly (during ca 5 minutes) while processing well (Ystral speed 3-5) for totally 15 minutes.
SPF: well over 30 (SPF in vitro 49 +/− 3)
UVA: fulfills "Australian Standard"

Example 16

Fluid Foundation Using Granlux™ Melanin Mimic™ TB Concentrate

For making this composition there was used a semi-composition Granlux™ Melanin Mimic™ which is a formula imitating the UV protection of natural melanin. Growth of micro-organisms (bacteria, fungi, yeast) was inhibited by a wood knot extract of 10 wt % mixture of phenolic compounds extracted from spruce knots in pentylene glycol (10 wt % of mixture of phenolic compounds and 90 wt % of pentylene glycol). This raw wood knot extract was used without further purification. Also betulonic acid originating to birch bark was used as an antimicrobial agent.

| Trade name/INCI | Amount (wt %) | Manufacturer |
|---|---|---|
| A | | |
| Magnesium aluminum silicate (Veegum K) | 0.70 | Vanderbilt |
| Xanthan gum (Rodicare) | 0.30 | Rhône Poulenc |
| 10% Extracted wood knot mixture in pentylene glycol | 6.00 | Granula Ltd |
| Glycerine | 4.00 | |
| Deionized water | q.s. | |

Wet the Xanthan gum in water + glycerine + 10 wt % polyphenolic wood knot mixture extracted from spruce knots into pentylene + 10 wt % Betulonic acid in propylene glycol. Homogenize with turboemulsifier and add Magnesium aluminum silicate while mixing, heat to 75° C.

| Trade name/INCI | Amount (wt %) | Manufacturer |
|---|---|---|
| B | | |
| Granlux ™ Melanin Mimic ™ | 27.50 | Granula Ltd |
| *Limnanthes alba*; | | |
| *Butyrospermum parkii* | 3.50 | The Fanning Co |
| (Fancol VB) | | |
| Glyceryl stearate | 0.80 | Th. Goldschmidt |
| (Tegin M) | | |
| Isopropyl myristate | 4.00 | |
| Isohexadecane | 10.00 | ICI |
| (Arlamol HD) | | |
| Stearic acid | 2.00 | |
| Dimethicone | 1.00 | Dow Corning |
| (Dow Corning 200 Fluid 100 cs) | | |
| Melt Phase B at 65° C., slowly homogenizing for ca 5 min, heat to 75° C. | | |
| B1 | | |
| Talcum | 1.00 | |
| Add Phase A to Phases B while homogenizing. As emulsion is formed, add Phases B1 and C slowly while continuing homogenizing. | | |
| C | | |
| Triethanolamine | 1.50 | |
| D | | |
| PPG 25 Laureth 25 | 0.20 | Vevy |
| (ADF Oleile) | | |
| At 40° C. add Phase D while homogenizing. Cool to room temperature while mixing. | | |

Characteristics:
pH: ca 7
Viscosity: 6.000
SPF: 21-24

Example 17

This product is good for protecting and curing the skin against UV and UV induced damage. It also gives some colour.

Soft Colored Cream (SCC/EM/98)

| INCI(Trade name) | Amount (%) | Manufacturer |
|---|---|---|
| A | | |
| Magnesium aluminum silicate | 0.50 | Vanderbilt |
| (Veegum K) | | |
| Xanthan gum | 0.50 | Rhône Poulenc |
| (Rodicare) | | |
| Propylene glycol | 6.00 | |
| 10% Betulonic acid in Glycerine | 4.00 | Granula Ltd |
| Deionized water | up to 100% | |
| Wet the Xanthan gum in water + betulonic acid in glycerine + propylene glycol. Homogenize with turboemulsifier and add Magnesium aluminum silicate while mixing, heat to 75° C. | | |
| B | | |
| Granlux ® EM-50 | 10.00 | Granula Ltd |
| *Limnanthes alba*; | | |
| *Butyrospermum parkii* | 3.50 | The Fanning Co |
| (Fancol VB) | | |
| Glyceryl stearate | 0.80 | Th. Goldschmidt |
| (Tegin M) | | |
| Isopropyl myristate | 4.00 | |
| Isohexadecane | 10.00 | ICI |
| (Arlamol HD) | | |
| Polydecene | 4.00 | Fortum |
| (Nexbase 2004 FG) | | |

| INCI(Trade name) | Amount (%) | Manufacturer |
|---|---|---|
| Polyhydroxystearic acid | 0.50 | ICI |
| (Arlacel P100) | | |
| Melt Phase B at 65° C., add Phase B1 slowly homogenizing for ca 5 min, heat to 75° C. | | |
| B1 | | |
| CI 77492 | 1.40 | Warner&Jenkinson |
| (Ariabel yellow) | | |
| CI 77491 + CI 77492 | 0.30 | Warner&Jenkinson |
| (Ariabel sienna) | | |
| CI 77491 + CI 77492 CI 77499 | 0.30 | Warner&Jenkinson |
| (Ariabel umber) | | |
| CI 77891 (Titanium dioxide) | 6.00 | Kemira |
| (Kemira AFDC) | | |
| Add Phase A to Phases B + B1 while homogenizing. As emulsion is formed, add Phase C while continuing homogenizing. | | |
| C | | |
| Talcum | 1.00 | |
| Aluminum starch octenylsuccinate | 3.00 | National Starch |
| (Dry-Flo PC) | | |
| D | | |
| PPG 25 Laureth 25 | 0.20 | Vevy |
| (ADF Oleile) | | |
| Propylene glycol; Diazolidinyl urea; Methyl paraben; Propylparaben | 1.00 | ISP |
| (Germaben II E) | | |
| At 40° C. add Phase D whilst homogenizing. Cool to room temperature while mixing. | | |

Note:
During the preparation the phase inversion temperature is clearly noticeable (PIT ca 40°) since the W/O system previously formed breaks into two phases: one liquid and one creamy. While continuing homogenization, the final emulsion (O/W) is easily obtained. The low value of PIT is not related to unstable behavior, in fact the formulation is still stable after 4 months at 42° C.

Characteristics:
pH: ca 7
Viscosity: 180.000 mPa s RVT Brookfield (5 rpm, 298 K, Helipath Stand T-D
SPF: 21-23 in vitro, UVA/UVB = 0.77

Example 18

A stick with UV protection of SPF 15 was made from semi-composition of Granlux CCA-50, which includes mainly physical filter for UV protection, beeswax and carnauba wax. Large-scale protection against micro-organisms (bacteria, yeast, fungi) is achieved by a powdered knot mixture including compound mixture and originating to pulverized spruce and/or pine knots.

SPF 15 Stick

| | | |
|---|---|---|
| Hydrogenated Vegetable Oil | 15.0 | Aarhus Olie |
| (Cremeol HF-52) | | |
| Vegetable Oil (Cremeol PS-6) | 68.0 | Aarhus Olie |
| Candelilla wax | 6.0 | |
| Powdered knot mixture of spruce and/or pine wood knot | 1.0 | Oy Granula Ab, Ltd |
| Granlux CCA-50 | 10.0 | Oy Granula Ab, Ltd |
| Heat ingredients to 75-80° C. Mix until uniform. Cool to 50° C. Pour into moulds. | | |

Characteristics:
SPF: 13-15 in vitro
UVA/UVB ratio 0.56

Example 19

A stick with UV protection of SPF 30 was made from semi-composition of Granlux CCA-50, which includes mainly physical filter for UV protection, beeswax and carnauba wax. Large-scale protection against micro-organisms (bacteria, yeast, fungi) is achieved by a powdered knot mixture including compound mixture and originating to pulverized spruce and/or pine knots.

Formula: SPF 30 Stick

| Trade name/INCI | wt % | |
|---|---|---|
| Beeswax (*Cera alba*) | 12.0 | |
| Caprylic Capric Triglycerides | 12.5 | |
| Macadamia nut oil | 9.5 | |
| Cetearyl alcohol | 7.5 | Henkel |
| Petrolatum | 36.5 | |
| Granlux CCA-50 | 20.0 | Oy Granula Ab, Ltd |
| Powdered knot mixture of spruce and/or pine wood knot | 2.0 | Oy Granula Ab, Ltd |

Heat ingredients to 75-80° C. Mix until uniform. Pour into molds.

Characteristics:
SPF: 28-30 in vitro

Example 20

Sun Protection Gel

| Trade name/INCI | wt % |
|---|---|
| A | |
| Uvinul MC 80/Octyl Methoxycinnamate | 8.00 |
| Uvinul N 539 T/Octocrylene | 5.00 |
| Uvinul M 40/Benzophenone-3 | 2.00 |
| Parsol 1789/Butyl Methoxydibenzoylmethane | 0.80 |
| Vitamin E Acetate/Tocopheryl Acetate | 2.00 |
| Cremophor RH 410/PEG-40 Hydrogenated Castor Oil | 1.00 |
| Perfume | q.s. |
| B | |
| Pemulen TR-1/Acrylates/ C10-30 Alkyl Acrylate Crosspolymer | 0.30 |
| Carbopol 940/Carbomer | 0.20 |
| 10% Extracted Spruce and/or Pine knot mixture in Dioctyl Glycol | 5.00 (Granula Ltd) |
| Edeta BD/EDTA | 0.20 |
| Water | 75.30 |
| C | |
| Sodium Hydroxide | 0.20 |

Production
Dissolve phase A. Stir phase B into phase A whilst homogenizing, then neutralize with phase C and homogenize again.
Viscosity: approx. 5 500 mPa s (Haake Viscotester VT-02)
pH-value: approx. 9.1.

Example 21

Sunscreen Foam

The Sunscreen Foam contains also various organic compounds (Octyl Methoxycinnamate, Octyl Triazone and 4-Methylbenzylidene Camphor) which have protective properties against UVA and UVB radiation (absorbing UV radiation in critical wavelength and also trapping free radicals induced by UV radiation). Phenolic compound mixture was extracted from particles of knot wood of spruce and/or pine into pentylene glycol. The amount of phenolic compound mixture in final composition was 0.05 wt %. This phenolic compound mixture contributes in capturing free radicals induced by UVA radiation and also capturing free radicals induced by particles of these organic UV-protective compounds.

| Trade name/INCI | wt % |
|---|---|
| A | |
| Cremophor A 25/Ceteareth-25 | 5.00 |
| Palmitic Acid | 2.00 |
| Finsolv TN/Alkyl Benzoate | 5.00 |
| Witconol APM/PPG-3 Myristyl Ether | 5.00 |
| Uvinul MC 80/Octyl Methoxycinnamate | 6.00 |
| Uvinul T 150/Octyl Triazone | 0.50 |
| Uvinul MBC 95/4-Methylbenzylidene Camphor | 1.00 |
| B | |
| 10% Extracted Spruce and/or Pine knot mixture in Pentylene Glycol | 5.00 |
| Water | 70.30 |
| C | |
| Triethanolamine | 0.20 |
| D | |
| Perfume | q.s. |

Production
Heat phases A and B separately to about 80° C. Stir phase B into phase A whilst homogenizing. Stir in phase C and rehomogenize. Cool to about 40° C., add phase D and homogenize again.
Filling: 90% active ingredient
10% propane/butane 3.5 bar (20° C.).

Example 22

Animal Feed

Into soybean feed, there was added by spraying a raw wood knot extract, with an alcohol content of 90-95 wt %, and wood knot extract with compound mixture 5-10 wt %. The wood knot extract was obtained by extracting either a wooden chips of Norway spruce knotwood with alcohol (extracted knot mixture from spruce), or wooden chips from Norway spruce and pine knotwood with alcohol, which extracted mixed knot mixture included a compound mixture containing lignans and stilbenes.

Example 23

A feed composition for domestic mammals comprising spruce knot extract or pine knot extract or any mixture of them at a concentration of 0, 1-15 wt % and at least one component selected from a group consisting of meat and bone meal, blood meal, poultry byproduct meal, tallow, wheat middlings, roughage products, oat groats, alfalfa meal, bakery by-products, brewers dried grains, distillers dried grains and solubles, citrus pulp, beet pulp, corn gluten feed, corn gluten meal, cottonseed meal, fish meal, hominy feed, kelp meal, linseed meal, sunflower meal, canola and rapeseed meal, and rice bran.

Example 24

This is a example of a semi finished UV-protection product containing wood knot extract.

Wood knot extract, such as spruce knot extract or pine knot extract or any mixture of them, at a concentration of 0, 1-15 wt % mixed in any UV-protection concentrate, such as GranLux-products (produced by Granula Ltd).

| | |
|---|---|
| Wood knot extract | 2-10% |
| GranLux concentrate | 98-90% |

In the examples 3-24, the term extracted wood knot mixture or extracted knot mixture or wood knot extract refers to the extracted solution containing (poly)phenolic compounds including compound mixture according to the invention, which mixture is obtained by extracting stem knotwood chips in alcohol and/or glycol. A powdered wood knot mixture of powdered knot mixture or wood knot powder in turn refers to a corresponding pulverized mixture, which is obtained by pulverizing stem knotwood chips. Mixed extracts of pine and spruce contained 1 part by volume of extracted knot mixture from pine, and 4 parts by volume of extracted knot mixture from spruce. Powdered knot mixtures originating from spruce and pine contained 1 part by weight pulverized pine and 3 parts by weight pulverized spruce.

As presented in example 6 the compound mixtures according to invention can also be used as a wound healing agent in various cosmetic compositions.

In examples 1-24 powdered or extracted mixed wood knot mixtures originating from spruce knotwood and pine knotwood the composition of compound mixtures were blends of phenolic compounds indicated in table 1 (pine) and table 2A (spruce). Powdered or extracted wood knot mixtures originating from spruce knotwood the composition of phenolic compound mixture was similar indicated in table 2A. However it should be understood that instead of pine and spruce species whose composition of phenolic compound mixture is indicated in table 1 and 2A it can also other pine and spruce species be used, for example those whose composition of phenolic compound mixture is given in table 3B.

The invention claimed is:

1. A method for preparing a composition, comprising:
   (i) pulverizing and/or extracting wood material with an organic solvent to obtain a wood extract, the extracted wood material comprising:
      (a) 50-99.9 wt % of at least two different compounds selected from the group consisting of: lignans, stilbenes, juvabiones, flavonoids, betulin, betulonic acid, betulinic acid, and betuloinic acid, and ester derivatives, ether derivatives or stereoisomers thereof; and
      (b) 1-31 wt % of oligomers of lignans, stilbenes, juvabiones or flavonoids,
      wherein at least one compound of said two different compounds is selected from the group consisting of: 7-hydroxymatairesinol, conidendrin, conidendric acid, alpha-conidendrin, alpha-conidendric acid, isohydroxymatairesinol, cyclolariciresinol, secoisolariciresinol, anhydrosecoisolariciresinol and stilbenes, and ester derivatives, ether derivatives or stereoisomers thereof;
   (ii) measuring cytotoxicity of said wood extract, the cytotoxicity being measured with a HaCat cell culture after a 24 hour incubation period;
   (iii) selecting a wood extract having a cytotoxicity at 0.1-5 wt % in ethanol that is lower than the cytotoxicity of 0.02-0.1 wt % butylated hydroxytoluene (BHT) in ethanol; and
   (iv) mixing said selected wood extract with a carrier agent.

2. The method according to claim 1, wherein the amount of the selected wood extract is such that the cytotoxicity of the wood extract in ethanol is lower than the cytotoxicity of 0.01-0.05 wt % BHT in ethanol.

3. The method according to claim 1, wherein the oligomers are oligolignans.

4. The method according to claim 1, wherein the wood extract is used as such, without refining, in the composition.

5. The method according to claim 1, wherein said extracted wood material comprises:
   70-80 w % hydroxymatairesinol,
   3-6 w % secoisolariciresinol,
   4-7 w % conidendrin,
   1-3 w % lariciresinol,
   2-5 w % liovile, and
   5-8 wt % other lignans.

6. The method according to claim 1, wherein the wood extract is obtained from wood material of at least two different wood species, and said at least two different compounds comprises lignans and stilbenes.

7. The method according to claim 6, wherein the two wood species are pine and spruce, 50-99.9% of the lignans being obtained from spruce knot material or spruce stemwood material adjacent to knots, and 0.1-50% of the lignans being obtained from pine knot material or pine stemwood material adjacent to knots.

8. The method according to claim 1, wherein the at least two different compounds are selected from the group consisting of:

Lignans:
matairesinol, hydroxymatairesinol, oxomatairesinol, didemethyl matairesinol, isohydroxymatairesinol, epi-isohydroxymatairesinol, 7S,8R hydroxymatairesinol stereoisomers, 8'R-hydroxymatairesinol and 7R,8R,8'R-allohydroxymatairesinol, and stereoisomers, ester derivatives or ether derivatives thereof, secoisolariciresinol, isolariciresinol, lariciresinol, pinoresinol, dimethyl secoisolariciresinol, 7-hydroxysecoisolariciresinol, cyclolariciresinol, and stereoisomers, ester derivatives or ether derivatives thereof, nortrachelogenin and stereoisomers, ester derivatives or ether derivatives thereof, enterolactone and stereoisomers, ester derivatives or ether derivatives thereof, conidendrin, α-conidendrin, α-conidendric acid, conidendric acid, and ester derivatives or ether derivatives thereof, lignan A and stereoisomers, ester derivatives or ether derivatives thereof, and liovile and stereoisomers, ester derivatives or ether derivatives thereof;

Juvabiones:
juvabiones and stereoisomers, ester derivatives or ether derivatives thereof;

Stilbenes:
pinosylvin, dihydropinosylvin, pinosylvin monomethyl ether, dihydropinosylvin monomethyl ether, resvatrol, astringin, isorhapontine, and stereoisomers, ester derivatives or ether derivatives thereof;

Flavonoids:
pinosembrin, catechin, pinobanxin, kaempferol, dihydrokaempferol, taxifolin, naringenin, teracasidine, ketoteracasidine, isoteracasidine, melacasidine, isomelacasidine and stereoisomers, ester derivatives or ether derivatives thereof, as well as glycosidized forms of polyphenolic compounds mentioned above and their oligomers, trimers and tetramers, and betulin, betulonic acid, betulinic acid, betuloinic acid and ester derivatives thereof.

9. The method according to claim 1, wherein said wood material is wood knot material or stemwood material adjacent to knots, and the wood extract is obtained by extracting the wood material with an organic hydrophilic solvent, said hydrophilic solvent forming part of the carrier agent of the composition.

10. The method according to claim 9, wherein the hydrophilic solvent is lower alkyl carbonyl, monovalent alcohol, multivalent alcohol or a mixture thereof.

11. The method according to claim 10, wherein said multivalent alcohol is selected from the group consisting of: lower alkyl diode, propyl glycol, butyl glycol, pentyl glycol, octyl glycol, lower alkyl triol, and esters thereof.

12. The method according to claim 1, wherein the wood extract is obtained by first extracting the wood material with a hydrocarbon, and then extracting with an alcohol or organic lower alkyl carbonyl compound, said alcohol or alkyl carbonyl compound forming part of the carrier agent of the composition.

13. The method according to claim 12, wherein said hydrocarbon is a lower alkane, hexane or heptane.

14. The method according to claim 12, wherein said solvent and said carrier agent contains a hydrocarbon-based solution, a ketone, an organic anion-cation solution, an ionogenic solution, or an ester of a trivalent alcohol.

15. The method according to claim 1, wherein the composition is a cosmetic composition, a food industry composition, an animal feed composition, a technical composition or a packing material composition, and said composition is administered to a mammal or gets into contact with a mammal.

16. The method according to claim 15, wherein the composition is a homogeneous mixture, a homogeneous solution, a colloidal dispersion, a paste-like solution, an emulsion, a microemulsion, a nanoemulsion, a heterogeneous mixture or a suspension.

17. The method according to claim 1, further comprising adding a surface agent to the composition.

18. The method according to claim 17, wherein the surface agent is selected from the group consisting of: tenside, emulsifier, cationic surface active agent, anionic surface active agent, amphoteric surface active agent, non-ionogenic surface active agent, cetearyl pyridium chloride, bentsalkonium chloride, cetearyl glycoside, lower alcoxilated glycosides, micelle-forming agents, and lecithin.

19. The method according to claim 1, further comprising adding betulin, betulinic acid, betulonic acid, betuloinic acid or their ester derivatives, obtained from birch bark, to the composition.

20. The method according to claim 1, further comprising adding a synthetic or natural antioxidant to the composition.

21. The method according to claim 20, wherein the antioxidant is selected from the group consisting of: agents naturally occurring on mammal skin, synthetic antioxidants, vitamins, A, B, C, D and E vitamins, microbicidic agents that have antioxidative effects, enzymes, or enzyme Q10, antioxidants obtained from plants or from green tea, melamine and synthetic melamine-like agents, antioxidant occurring in green tea, and antioxidants occurring in fruits of an eucalyptus tree.

22. The method according to claim 1, the composition comprising a wood extract having UV-protective properties and a carrier agent, wherein the wood extract provides the composition with an in vivo protective factor against UV radiation.

23. The method according to claim 22, wherein the composition further comprises an organic or inorganic UV-protective agent having protective properties against UVA and UVB radiation, the composition providing enhanced in vivo protective activity against UV-radiation compared to in vitro protective activity, and the composition includes said wood extract in an amount of 0.3-0.5 wt %.

24. The method according to claim 23,
wherein the carrier agent is a cream-like W/O or O/W carrier, and the composition further comprises an emulsifier, emollient, dispersion agent, perfume and vitamins,
wherein the composition controls a cytotoxicity level of effective agents in the composition.

25. The method according to claim 1,
wherein the composition further comprises a finely divided inorganic UV-protective agent having protective properties against UVA and UVB radiation, and
said compound mixture is included into a coating of the inorganic UV-protective agent, said coating inhibiting induction of free radicals from the inorganic UV-protective agent.

26. The method according to claim 25, wherein the finely divided inorganic UV-protective agent is titanium oxide, iron oxide, zinc oxide or cerium oxide, the oxide particles of which are coated with a silica compound, a metal oxide or aluminum oxide.

27. The method according to claim 26, further comprising dispersing the finely divided inorganic UV-protective agent coated with the silica compound, metal oxide or aluminum oxide in an oil phase prior to including the UV protective agent in the composition.

28. The method according to claim 25, wherein the UV-protective agent protects skin against UV radiation similar to that of natural melanin on the skin.

29. The method according to claim 28, wherein,
the finely divided inorganic UV-protective agent is coated with a silica compound or with a metal oxide,
the carrier agent is a liquid W/O or O/W carrier, and
the composition further comprises emulsifier, additives, viscosity regulator, moisturizer, and/or emollient.

30. The method according to claim 25, wherein the composition is a sun protection composition comprising:
an inorganic finely divided UV-protective agent coated with a composition comprising the compound mixture and at least one of a silica compound, a metal oxide or aluminum oxide,
a liquid, cream-like or mist-like carrier agent,
emulsifier, and
additives.

31. The method according to claim 1, the composition comprising a wood extract having antioxidative and/or free-radical capturing properties, further comprising a synthetic or natural antioxidant,
wherein the wood extract has similar antioxidative properties as said synthetic or natural antioxidant but a higher free-radical capture rate than said synthetic antioxidant or better stability than said natural antioxidant.

32. The method according to claim 31, wherein said natural antioxidant is a natural vitamin and the wood extract has similar antioxidative properties as said natural vitamin but higher temperature and/or UV light resistance than said natural vitamin.

33. The method according to claim 31, wherein the composition comprises: antioxidants or vitamins, the wood extract, colloidal W/O or O/W carrier agent, emulsifier, additives, inorganic UV protector agents, and a viscosity regulator.

34. A method for preparing a semi-finished composition comprising a compound mixture, whereby said semi-finished composition can be converted to an end composition by adding solvent therein, wherein the compound mixture is obtained by:
- (i) pulverizing and/or extracting wood material to obtain an extract containing a blend of compounds comprising:
  - (a) 50-99.9 wt of at least two different compounds selected from the group consisting of: lignans, stilbenes, juvabiones flavonoids, betulin, betulonic acid, betulinic acid, and betuloinic acid, and ester derivatives, ether derivatives or stereoisomers thereof; and
  - (b) 1-31 wt % of oligomers of lignans, stilbenes, juvabiones or flavonoids,
  - and wherein at least one compound of said two different compounds is selected from the group consisting of: 7-hydroxymatairesinol, conidendrin, conidendric acid, alpha-conidendrin, alpha-conidendric acid, isohydroxymatairesinol, cyclolariciresinol, secoisolariciresinol, anhydrosecoisolariciresinol and stilbenes, and ester derivatives, ether derivatives or stereoisomers thereof,
- (ii) measuring cytotoxicity of said extracted wood material, the cytotoxicity being measured with a HaCat cell culture after a 24 hour incubation period;
- (iii) selecting an extract having a cytotoxicity at a concentration of 0.1-5 wt % in ethanol that is lower than the cytotoxicity of 0.02-0.1 wt % butylated hydroxytoluene (BHT) in ethanol;
- (iv) mixing said selected extracts to form a compound mixture; and
- (v) mixing the compound mixture with a carrier agent, at a concentration of 0.1-5 wt %.

35. The method for preparing the semi-finished composition according to claim 34, said semi-finished composition comprising a compound mixture having antioxidative and/or free-radical capturing properties, a carrier agent and a synthetic or natural antioxidant or vitamin,
   wherein the compounds of said compound mixture are additionally selected to have similar antioxidative properties as said synthetic or natural antioxidant but higher free-radical capture rate than said synthetic antioxidant or better stability than said natural antioxidant.

36. The method for preparing the semi-finished composition according to claim 34, said semi-finished composition comprising an effective agent comprising a compound mixture having antioxidative and/or free-radical capturing properties, a carrier agent and a finely divided inorganic UV-protector agent, whereby said composition is administered to a mammal or gets into contact with a mammal,
   wherein the compounds of said compound mixture are additionally selected to be capable of inhibiting induction of free radicals from particles originating from said finely divided inorganic UV-protector agent when said compound mixture is included into a coating of said finely divided inorganic UV-protector agent.

37. A method for preparing a composition for use in cosmetics, comprising:
- (i) extracting wood material with an organic hydrophilic solvent;
- (ii) measuring cytotoxicity of the extract, the cytotoxicity being measured with a HaCat cell culture after a 24 hour incubation period, the extracted wood material comprising:
  - (a) 50-99.9 wt % of at least two different compounds selected from the group consisting of: lignans, stilbenes, juvabiones, flavonoids, betulin, betulonic acid, betulinic acid, betuloinic acid, and ester derivatives, ether derivatives or stereoisomers thereof,
  - wherein at least one compound of said two different compounds is selected from the group consisting of: 7-hydroxymatairesinol, conidendrin, conidendric acid, alpha-conidendrin, alpha-conidendric acid, isohydroxymatairesinol, cyclolariciresinol, secoisolariciresinol, anhydrosecoisolariciresinol, stilbenes, and ester derivatives, ether derivatives or stereoisomers thereof; and
  - (b) 1-31 wt % of oligomers of lignans, stilbenes, juvabiones or flavonoids;
- (iii) selecting extracts having a cytotoxicity at a concentration of 0.1-5 wt % in ethanol that is lower than the cytotoxicity of 0.02-0.1 wt % butylated hydroxytoluene (BHT) in ethanol;
- (iv) combining the selected extracts to prepare a compound mixture;
- (v) mixing said compound mixture with a carrier agent.

38. The method according to claim 37, wherein the hydrophilic solvent comprises a monovalent, bivalent or trivalent lower alkyl alcohol, or a mixture thereof.

39. The method according to claim 37, wherein the hydrophilic solvent comprises ethanol.

40. The method according to claim 37, comprising extracting the wood material first with a hydrocarbon, and then with an alcohol or organic lower alkyl carbonyl compound.

41. The method according to claim 37, wherein the wood material comprises stemwood and/or knotwood from pine and/or spruce.

42. The method according to claim 41, wherein the wood material further comprises birch bark.

* * * * *